(12) United States Patent
Zhang et al.

(10) Patent No.: US 12,718,904 B2
(45) Date of Patent: Aug. 25, 2026

(54) ARTIFICIAL INTELLIGENCE-BASED COMPOUND PROCESSING METHOD AND APPARATUS, DEVICE, STORAGE MEDIUM, AND COMPUTER PROGRAM PRODUCT

(71) Applicants: TENCENT TECHNOLOGY (SHENZHEN) COMPANY LIMITED, Shenzhen (CN); ZHEJIANG UNIVERSITY, Hangzhou (CN)

(72) Inventors: Xujun Zhang, Shenzhen (CN); Benben Liao, Shenzhen (CN); Shengyu Zhang, Shenzhen (CN); Tingjun Hou, Shenzhen (CN)

(73) Assignees: TENCENT TECHNOLOGY (SHENZHEN) COMPANY LIMITED, Shenzhen (CN); ZHEJIANG UNIVERSITY, Hangzhou (CN)

( * ) Notice: Subject to any disclaimer, the term of this patent is extended or adjusted under 35 U.S.C. 154(b) by 489 days.

(21) Appl. No.: 18/494,372

(22) Filed: Oct. 25, 2023

(65) Prior Publication Data

US 2024/0055071 A1 Feb. 15, 2024

Related U.S. Application Data

(63) Continuation of application No. PCT/CN2022/093297, filed on May 17, 2022.

(30) Foreign Application Priority Data

Jun. 23, 2021 (CN) ......................... 202110696118.2

(51) Int. Cl.

*G16B 15/30* (2019.01)
*G06N 3/0455* (2023.01)

(Continued)

(52) U.S. Cl.

CPC ........... *G16B 15/30* (2019.02); *G06N 3/0455* (2023.01); *G06N 3/063* (2013.01); *G16B 40/20* (2019.02);

(Continued)

(58) Field of Classification Search

CPC ...... G16B 15/30; G16B 40/20; G06N 3/0455; G06N 3/063; G06N 3/042; G06N 3/047;

(Continued)

(56) References Cited

U.S. PATENT DOCUMENTS 6,185,506 B1 * 2/2001 Cramer .................. G16C 20/30 702/30
8,428,885 B2 * 4/2013 Kunert ................... G16C 20/64 702/19

(Continued)

FOREIGN PATENT DOCUMENTS

CN 111199779 A 5/2020
CN 111462833 A 7/2020

(Continued)

OTHER PUBLICATIONS

The World Intellectual Property Organization (WIPO) International Search Report for PCT/CN2022/093297 Aug. 17, 2022 7 Pages (including translation).

(Continued)

*Primary Examiner* — Jorge A Casanova

(74) *Attorney, Agent, or Firm* — Anova Law Group, PLLC

(57) ABSTRACT

An artificial intelligence-based compound processing method and apparatus, an electronic device, a computer-readable storage medium, and a computer program product relates to an artificial intelligence technology. The method includes obtaining an active compound for a target protein; performing compound generation processing on an attribute (Continued)

property of the active compound to obtain a first candidate compound; performing molecular docking processing on the active compound and the target protein to obtain molecular docking information respectively corresponding to a plurality of molecular conformations of the active compound; screening the plurality of molecular conformations based on the molecular docking information respectively to identify a second candidate compound corresponding to the active compound; and constructing a compound library for the target protein based on the first candidate compound and the second candidate compound.

18 Claims, 16 Drawing Sheets

(51) Int. Cl.
*G06N 3/063* (2023.01)
*G16B 40/20* (2019.01)
*G16C 20/30* (2019.01)
*G16C 20/50* (2019.01)
*G16C 20/60* (2019.01)

(52) U.S. Cl.
CPC ............ *G16C 20/30* (2019.02); *G16C 20/50* (2019.02); *G16C 20/60* (2019.02)

(58) Field of Classification Search
CPC .......... G06N 3/048; G06N 3/084; G06N 3/09; G06N 3/0442; G06N 3/0475; G06N 3/088; G06N 3/044; G06N 3/061; G06N 3/08; G16C 20/30; G16C 20/50; G16C 20/60; G16C 20/70; G16C 10/00; G16C 20/64; G16C 20/90
See application file for complete search history.

(56) References Cited

U.S. PATENT DOCUMENTS 9,310,364 B1 * 4/2016 Edwards ................ G16C 20/60
11,127,488 B1 * 9/2021 Bajpai .................... G16C 20/50
12,367,397 B2 * 7/2025 Hoffman ............... G06F 16/245
12,542,194 B1 * 2/2026 Lewy ..................... G16B 15/30
2008/0133434 A1 * 6/2008 Asar ...................... G06N 20/10 706/12
2011/0169937 A1 * 7/2011 McLaughlin .......... G16C 20/70 382/133
2021/0057050 A1 * 2/2021 Zavoronkovs ....... C07D 471/10
2021/0104331 A1 * 4/2021 Mysore .................. G16C 20/70
2022/0130487 A1 4/2022 Yang et al.
2022/0165360 A1 * 5/2022 Lee ...................... G06N 3/0495
2023/0139642 A1 * 5/2023 Yao ....................... G06F 40/289 704/9
2023/0335231 A1 * 10/2023 Abdallah ............... G06N 3/088
2024/0055071 A1 2/2024 Zhang et al.
2024/0177012 A1 * 5/2024 Sultan .................... G16B 15/30
2025/0118391 A1 * 4/2025 Yuan ...................... G16B 35/20
2025/0166744 A1 * 5/2025 Bean ...................... G16C 20/80
2025/0172540 A1 * 5/2025 Kilgore .................... G06N 5/01
2025/0201336 A1 * 6/2025 Belyanskaya .......... G16B 35/00
2025/0372196 A1 * 12/2025 Gniewek ................ G06N 3/045
2025/0391518 A1 * 12/2025 Beaini .................... G16C 20/70
2026/0004888 A1 * 1/2026 White .................... G16C 20/30
2026/0088138 A1 * 3/2026 Van Hoorn ............ G16C 20/50

FOREIGN PATENT DOCUMENTS

CN 112053742 A 12/2020
CN 112201313 A 1/2021
CN 113436686 A 9/2021
WO 2021103516 A1 6/2021

OTHER PUBLICATIONS

The State Intellectual Property Office of the People's Republic of China (SIPO) Office Action 1 for 202110696118.2 May 18, 2023 7 Pages (including translation).
P. J. Ballester et al.; A machine learning approach to predicting protein-ligand binding affinity with applications to molecular docking. Bioinformatics 2010, 26, 1169-1175.
D. Xue et al., Advances and challenges in deep generative models for de novo molecule generation. WIREs Computational Molecular Science 2019, 9, e1395.
N.Huang et al., Benchmarking Sets for Molecular Docking. J. Med. Chem. 2006, 49, 6789-6801.
S. M. Vogel et al., DEKOIS: demanding evaluation kits for objective in silico screening—a versatile tool for benchmarking docking programs and scoring functions. J Chem Inf Model 2011, 51, 2650-65.
P.-C. Kotsias et al., Direct steering of de novo molecular generation with descriptor conditional recurrent neural networks. Nature Machine Intelligence 2020, 2, 254-265.
M. M. Mysinger et al., Directory of Useful Decoys, Enhanced (DUD-E): Better Ligands and Decoys for Better Benchmarking. J. Med. Chem. 2012, 55, 6582-6594.
D. Rogers et al., Extended-Connectivity Fingerprints. Journal of Chemical Information and Modeling 2010, 50, 742-754.
C. Shen et al., From machine learning to deep learning: Advances in scoring functions for protein-ligand docking. WIREs Computational Molecular Science 2020, 10, e1429.
F. Imrie et al., Generating Property-Matched Decoy Molecules Using Deep Learning. Bioinformatics (Oxford, England) 2021.
J. Sieg et al., In Need of Bias Control: Evaluating Chemical Data for Machine Learning in Structure-Based Virtual Screening. Journal of Chemical Information and Modeling 2019, 59, 947-961.
V.-K. Tran-Nguyen et al., LIT-PCBA: An Unbiased Data Set for Machine Learning and Virtual Screening. Journal of Chemical Information and Modeling 2020.
M. A. Khamis et al., Machine learning in computational docking. Artificial Intelligence in Medicine 2015, 63, 135-152.
S. G. Rohrer et al., Maximum Unbiased Validation (MUV) Data Sets for Virtual Screening Based on PubChem Bioactivity Data. Journal of Chemical Information and Modeling 2009, 49, 169-184.
R. X. Wang et al., The PDBbind database: Collection of binding affinities for protein-ligand complexes with known three-dimensional structures. J. Med. Chem. 2004, 47, 2977-2980.
I. Wallach et al., Virtual decoy sets for molecular docking benchmarks. J Chem Inf Model 2011, 51, 196-202.

* cited by examiner

ARTIFICIAL INTELLIGENCE-BASED COMPOUND PROCESSING METHOD AND APPARATUS, DEVICE, STORAGE MEDIUM, AND COMPUTER PROGRAM PRODUCT

RELATED APPLICATIONS

This application is a continuation application of PCT Application No. PCT/CN2022/093297, filed on May 17, 2022, which in turn claims priority to Chinese Patent Application No. 202110696118.2, filed on Jun. 23, 2021. The two applications are both incorporated by reference in their entirety.

FIELD OF THE TECHNOLOGY

This application relates to a smart medical technology, and in particular, to an artificial intelligence-based compound processing method and apparatus, an electronic device, a computer-readable storage medium, and a computer program product.

BACKGROUND OF THE DISCLOSURE

Artificial intelligence (AI) is a comprehensive technology of computer science. It is to study the design principles and implementation methods of various smart machines, to enable the machines to have the functions of perception, reasoning, and decision-making. The artificial intelligence technology is a comprehensive subject, which involves a wide range of fields, such as a natural language processing technology and machine learning/deep learning, etc.

Virtual screening is to predict the binding affinity of a compound database for a specific target by the artificial intelligence technology, to perform compound screening to obtain a lead compound for a specific target. Compared with biological experiments, virtual screening has the advantages of low cost and high efficiency. A scoring function in virtual screening is constructed and evaluated based on a compound data set.

However, the compound data set in the related art has hidden biases (for example, a domain bias or a causal bias). This causes virtual screening to have a prediction bias, and subsequent high-efficiency compound screening cannot be performed.

SUMMARY

An embodiment of this application provides an artificial intelligence-based compound processing method and apparatus, an electronic device, a computer-readable storage medium, and a computer program product, which can eliminate a hidden bias of a compound library for subsequent accurate virtual screening based on a compound library without the hidden bias.

A technical solution in this embodiment is implemented as follows.

One aspect of this application provides an artificial intelligence-based compound processing method. The method includes obtaining an active compound for a target protein; performing compound generation processing on an attribute property of the active compound to obtain a first candidate compound; performing molecular docking processing on the active compound and the target protein to obtain molecular docking information respectively corresponding to a plurality of molecular conformations of the active compound; screening the plurality of molecular conformations based on the molecular docking information respectively to identify a second candidate compound corresponding to the active compound; and constructing a compound library for the target protein based on the first candidate compound and the second candidate compound.

Another aspect of this application provides an electronic device for compound processing. The electronic device includes: a memory, configured to store executable instructions; and a processor, configured to implement, when executing the executable instructions stored in the memory, the artificial intelligence-based compound processing method provided in this embodiment.

Another aspect of this application provides a non-transitory computer-readable storage medium storing executable instructions for implementing, when executed by a processor, the artificial intelligence-based compound processing method provided in this embodiment.

This embodiment of this application has the following beneficial effects.

By generating a first candidate compound having an attribute property, the structural diversity of a first candidate compound is increased, thereby alleviating a domain bias of a compound library constructed based on the first candidate compound. A second candidate compound corresponding to an active compound is screened by molecular docking, and a compound library for a target protein is constructed by combining the generated first candidate compound and the second candidate compound screened by molecular docking. The compound library constructed by combining the two candidate compounds can alleviate a noncausal bias relative to the compound library constructed by only one candidate compound, thereby enabling efficient screening of a valuable compound based on the compound library constructed subsequently.

DESCRIPTION OF EMBODIMENTS

Figure 1:
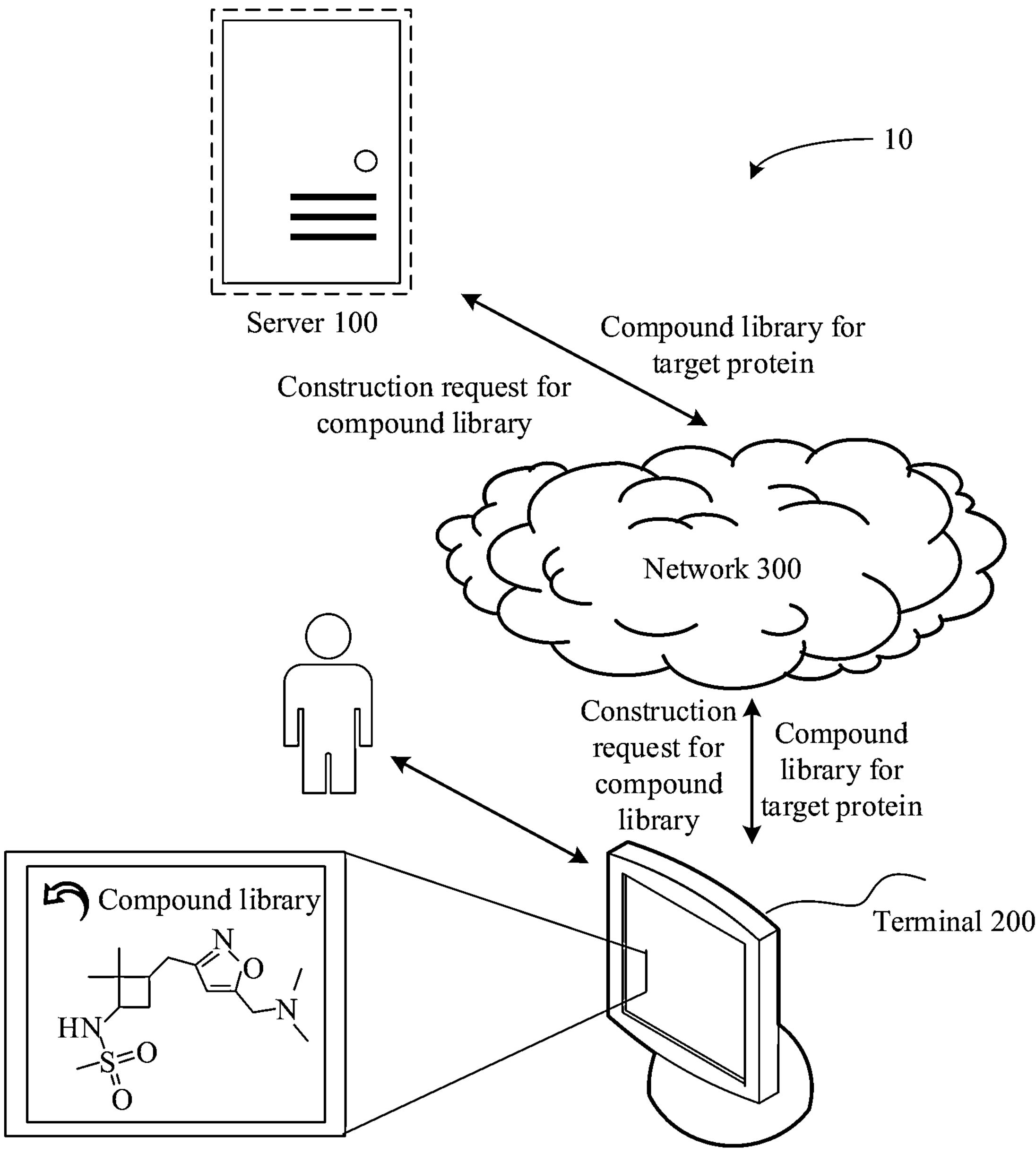
FIG. 1 is a schematic diagram of an application scenario of a medical system according to an embodiment of this application.

To make the objectives, technical solutions, and advantages of this application clearer, the following describes this application in further detail with reference to the accompanying drawings. The described embodiments are not to be considered as a limitation to this application. All other embodiments obtained by a person of ordinary skill in the art without creative efforts shall fall within the protection scope of this application.

The term "first/second" involved in the following description is only for distinguishing between similar objects and does not represent a particular sequence of the objects. It may be understood that "first/second" may be interchanged to particular sequences or orders if allowed to implement the embodiments of this application described herein in sequences other than that illustrated or described herein.

Unless otherwise defined, meanings of all technical and scientific terms used in this specification are the same as those usually understood by a person skilled in the art to which this application belongs. The terms used in this specification are for the purpose of describing the embodiments of this application only and are not intended to be limiting of this application.

Before the embodiments of this application are further described in detail, a description is made on nouns and terms in the embodiments of this application, and the nouns and terms in the embodiments of this application are applicable to the following explanations.

1) Simplified molecular input line entry specification (SMILES): a specification that explicitly describes molecular structures with strings of American standard code for information interchange (ASCII). A SMILES expression may describe a three-dimensional chemical structure with a string of characters. For example, the SMILES expression for cyclohexane ($C6H12$) is C1CCCCC1, that is, C1CCCCC1 is represented as cyclohexane.
2) Molecular conformation: Numerous specific images of atoms or groups of molecules arranged in a three-dimensional space.
3) Molecular docking: a process in which molecules undergo geometric matching and energy matching in protein pockets. The molecular docking usually includes two stages, namely conformation search and scoring function evaluation. The conformation search refers to changing the conformations of molecules by changing three-dimensional space coordinates of the molecules and dihedral angles between atoms. The scoring function evaluation is to use a scoring function to predict the binding affinity between specific protein ligand binding conformations.
4) Scoring function: a mathematical model for predicting the binding affinity between a protein and a ligand. The scoring function includes a force field-based scoring function, an experience-based scoring function, and a knowledge-based scoring function. Due to the rise of an artificial intelligence technology, AI-based scoring functions have made great progress. The training of scoring functions aims to accurately predict the binding affinity between a protein and a ligand by learning the differences in binding modes (interactions) between positive and negative samples in a data set.

The scoring function is constructed and evaluated dependently of the data set. The data set includes target protein files (PDB format), known active molecules bound to targets (SMILES, SDF, and MOL2 formats), decoys, known inactive molecules having low binding affinity to targets (SMILES, SDF, and MOL2 formats).

5) Attribute property: physicochemical properties of a compound, for example, molecular weight (MW), number of hydrogen bond acceptors (HBA), number of hydrogen bond donors (HBD), number of rotatable bonds (RB), lipid water partition coefficient (Log P), number of specific functional groups (HAL), and the like.
6) Decoys: due to the limitation of numerous drug targets and experimental costs, it is unlikely that the molecules in the database contain affinity data for all targets. Therefore, the molecules meeting the hypothesis are identified as inactive molecules for specific targets based on certain hypothesis, and these hypothetic inactive molecules are decoys.
7) Homology modeling: a three-dimensional structure of proteins is important information for understanding biological and physiological functions as well as drug design based on target structures. The homology modeling is a method for constructing the three-dimensional structure of the proteins based on an amino acid sequence of the proteins and using the three-dimensional structure of homologous proteins experimentally analyzed as a template. In drug design, a cavity in which small molecules and proteins are bound to regulate protein functions is called a binding pocket.
9) Hidden bias: biases caused by data set irrationality are manifested in very poor generalization performance of a scoring function model when these data sets with the hidden bias are used for scoring function training and testing, and the performance on the data sets deviates from the real performance. The hidden bias includes an artificial enrichment, an analogue bias, a domain bias, a noncausal bias, a false negative bias, and the like.

The artificial enrichment means that the distribution of physicochemical properties of positive and negative samples (organic compound molecules) in the data set is very different, so that the scoring function can well distinguish between active molecules and inactive molecules only through the data of the physicochemical properties. The scoring function trained on such a data set, although showing good predictive performance, does not have good generalization capability. That is to say, the scoring function does not correctly give the binding affinity between the protein and the ligand when used for prediction in real scenarios.

The analogue bias means that the inclusion of too many structurally similar compounds in the data set results in a higher performance of a model for testing.

The domain bias means that too few classes of compounds are contained in the data set. Although the scoring function learns from this class of compounds how to correctly distinguish between active and inactive compounds based on a partial protein-ligand interaction mode, the available domain of the scoring function is very narrow, and the binding affinity of molecules of only the compounds contained in the data set can be accurately predicted.

The noncausal bias means that the model learns some distribution of the data set during training to achieve better prediction accuracy, but does not learn from the biological mechanism of protein ligand binding. Therefore, the scoring function that learns the noncausal bias does not generalize well to other data sets. That is to say, the binding affinity cannot be correctly predicted on other data sets.

10) Extended connectivity fingerprints (ECFP): molecular fingerprints having a unique identifier assigned to each atom, the identifier being subject to several iterations. ECFP is circular fingerprints. In the definition thereof, a radius n (namely, number of iterations) needs to be set, and then an identifier for each atomic environment is calculated. ECFP2 is called in a case of n=1. ECFP4 is called in a case of n=2, and so on. For example, each atom is assigned with a 6-dimensional identifier (whether it is a hydrogen bond acceptor, whether it is a hydrogen bond donor, whether it is positively charged, whether it is negatively charged, whether it contains aromaticity, or whether it contains halogen). A functional class fingerprint (FCFP) containing pharmacophore information is obtained after several iterations.

In recent years, due to the development of the artificial intelligence technology, researchers introduce an artificial intelligence algorithm into the construction of the scoring function, and hope to improve the accuracy of the scoring function. The AI-based construction and evaluation of the scoring function will be dependent of the data set. However, the data set in the related art is designed for the construction and evaluation of the scoring function, and has the hidden bias. In the related art, there are three data sets, namely a data set based on real experimental data and a data set based on decoys. The data set based on real experimental data is a data set with a limited number of molecules obtained based on existing large molecule and protein databases. For example, the data set based on real experimental data may be PDBbind, Maximum Unbiased Validation (MUV), LIT-PCBA, or the like. Unlike the data set based on real experimental data, decoys in the data set based on decoys are collected from a database based on specific hypothesis. The data is more extensible. However, decoys do not contain experimental data and are not necessarily truly inactive molecules. For example, the data set based on decoys may be a directory of useful decoys (DUD), a directory of useful decoys enhanced (DUD-E), or demanding evaluation kits for objective in silico screening (DEKOIS).

However, the data set in the related art has the following problems. The noncausal bias exists in the data set based on decoys. Although the data sets based on real experimental data are unbiased, there are some problems in these data sets, such as extreme imbalance in the number of positive and negative samples, low scalability, and domain bias caused by a single chemical structure.

In order to solve the foregoing problems, an embodiment of this application provides an artificial intelligence-based compound processing method and apparatus, an electronic device, a computer-readable storage medium, and a computer program product, which can eliminate biases of a compound library to improve the accuracy of virtual screening.

The artificial intelligence-based compound processing method provided in this embodiment may be implemented by a terminal/server alone, or implemented by the terminal and the server cooperatively. For example, the terminal alone undertakes the artificial intelligence-based compound processing method described below, or the terminal transmits a construction request for a compound library (including target protein information) to the server, and the server performs the artificial intelligence-based compound processing method according to the received construction request for the compound library. A first candidate compound having an attribute property of a target protein is generated through a model, and a second candidate compound corresponding to an active compound is obtained through molecular docking. The first candidate compound and the second candidate compound are combined to construct a compound library for the target protein. Thus, a developer may rapidly perform subsequent molecular researches, analyses, and the like according to the constructed compound library.

The electronic device for compound processing provided in this embodiment may be various types of terminal devices or servers. The server may be an independent physical server, may also be a server cluster or distributed system composed of a plurality of physical servers, and may also be a cloud server providing a cloud computing service. The terminal may be a smartphone, a tablet computer, a notebook computer, a desktop computer, a smart speaker, a smartwatch, or the like, but is not limited thereto. The terminal and the server may be directly or indirectly connected in a wired or wireless communication manner. This is not limited by this application herein.

Taking a server as an example, the server may be, for example, a server cluster deployed on a cloud. An AI as a Service (AIaaS) is opened to users. An AIaaS platform may split several types of common AI services and provide independent or packaged services on the cloud. This service mode is similar to an AI theme mall. All users may access one or more artificial intelligence services provided using the AIaaS platform by means of an application programming interface.

For example, one of the artificial intelligence cloud services may be a compound processing service. That is to say, the server of the cloud encapsulates a compound processing program provided in this embodiment. A user invokes the compound processing service in the cloud service through the terminal (running a client, such as a drug screening client), so that the server deployed in the cloud invokes an encapsulated compound processing program. A first candidate compound having an attribute property of a target protein is generated through a model, and a second candidate compound corresponding to an active compound is obtained through molecular docking. The first candidate compound and the second candidate compound are combined to construct a compound library for the target protein. Subsequently, the service responds to a construction request for the compound library based on the compound library, and conducts molecular researches, analyses, and the according to the constructed compound library.

Referring to FIG. 1, FIG. 1 is a schematic diagram of an application scenario of a medical system 10 according to an embodiment of this application. A terminal 200 is connected to a server 100 via a network 300. The network 300 may be a wide area network or a local area network, or a combination of both.

The terminal 200 (running a client, such as a drug screening client) may be configured to obtain a construction request (including target protein information) for a compound library. For example, a developer inputs a target protein (for example, G protein-coupled receptors (GPCR)) through an input interface of the terminal 200, and then the construction request for the compound library is automatically generated.

In some embodiments, a compound processing plug-in may be embedded in the client run in the terminal for implementing, locally at the client, an artificial intelligence-based compound processing method. For example, after obtaining the construction request for the compound library, the terminal 200 invokes the compound processing plug-in to implement the artificial intelligence-based compound processing method. A first candidate compound having an attribute property of a target protein is generated through a model, and a second candidate compound corresponding to an active compound is obtained through molecular docking. The first candidate compound and the second candidate compound are combined to construct a compound library for the target protein. The construction request for the compound library is responded to subsequently based on the compound library.

In some embodiments, after obtaining the construction request for the compound library, the terminal 200 invokes a compound processing interface of the server 100 (which may be provided in the form of a cloud service, namely the compound processing service). The server 100 generates a first candidate compound having an attribute property of a target protein through a model, and obtains a second candidate compound corresponding to an active compound through molecular docking. The first candidate compound and the second candidate compound are combined to construct a compound library for the target protein. The construction request for the compound library is responded to subsequently based on the compound library. For example, for a drug screening application, a researcher inputs a target protein through an input interface of the drug screening client, automatically generates a construction request for a compound library, and invokes the compound processing interface of the server 100. A first candidate compound having an attribute property of a target protein is generated through a model, and a second candidate compound corresponding to an active compound is obtained through molecular docking. The first candidate compound and the second candidate compound are combined to construct a compound library for the target protein, and a neural network model is trained through the compound library for the target protein so as to realize a virtual screening function. Compounds with high binding affinity to the target protein are screened, whereby the developer can rapidly obtain active drug molecules from compounds with high binding affinity to the target protein subsequently.

Figure 2:
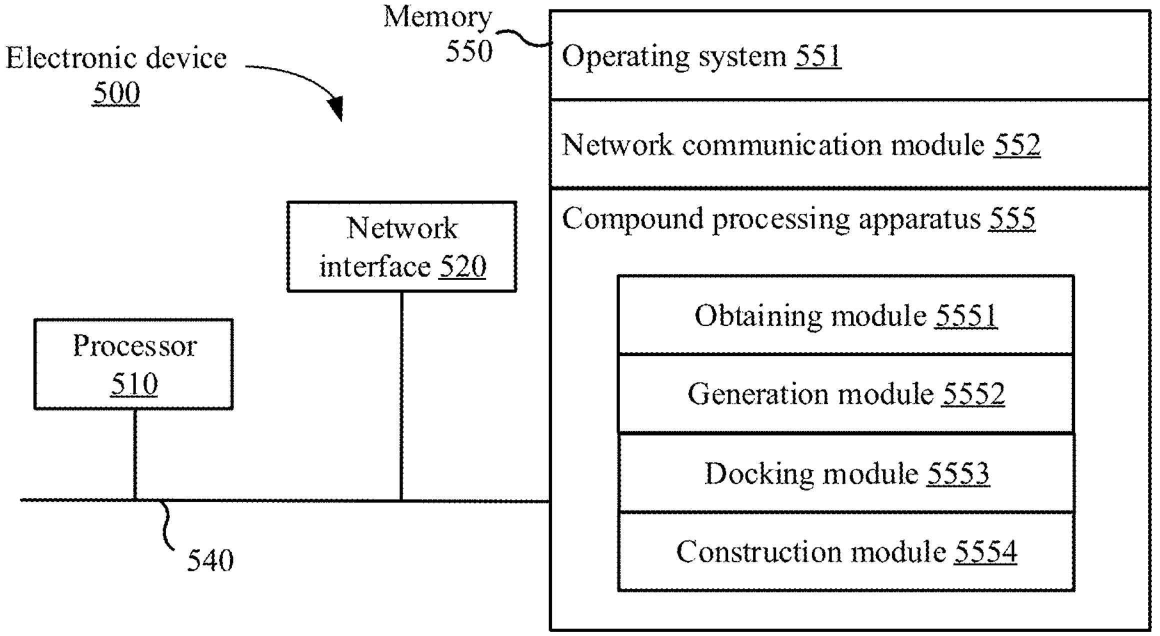
FIG. 2 is a schematic structural diagram of an electronic device for compound processing according to an embodiment of this application.

The structure of an electronic device for compound processing provided in this embodiment is described below. Referring to FIG. 2, FIG. 2 is a schematic structural diagram of an electronic device 500 for compound processing according to an embodiment of this application. Taking the electronic device 500 being a server as an example, the electronic device 500 for compound processing shown in FIG. 2 includes: at least one processor 510, a memory 550, and at least one network interface 520. Components in the electronic device 500 are coupled together by using a bus system 540. It may be understood that, the bus system 540 is configured to implement connection and communication between the components. In addition to a data bus, the bus system 540 further includes a power bus, a control bus, and a state signal bus. However, for ease of clear description, all types of buses in FIG. 2 are marked as the bus system 540.

The processor 510 may be an integrated circuit chip having signal processing capabilities, for example, a general processor, a digital signal processor (DSP), another programmable logic device, discrete gate or transistor logic device, or discrete hardware component, or the like. The general processor may be a microprocessor, any processor, or the like.

The memory 550 includes a volatile memory or a non-volatile memory, or may include both a volatile memory and a non-volatile memory. The non-volatile memory may be a read only memory (ROM), and the volatile memory may be a random access memory (RAM). The memory 550 described in this embodiment aims to include any suitable type of memory. The memory 550 may include one or more storage devices physically remote from the processor 510.

In some embodiments, the memory 550 is capable of storing data to support various operations. Examples of the data include programs, modules, and data structures or subsets or supersets thereof, as exemplified below.

An operating system 551 includes a system program for processing various basic system services and executing hardware-related tasks, such as a framework layer, a core library layer, and a driver layer, for realizing various basic services and processing hardware-based tasks.

A network communication module 552 is configured to reach other computing devices via one or more (wired or wireless) network interfaces 520. The network interface 520 exemplarily includes: Bluetooth, wireless fidelity (WiFi), and universal serial bus (USB), and the like.

In some embodiments, a compound processing apparatus provided in this embodiment may be implemented in software, for example, may be the compound processing plug-in in the terminal as described above, and may be the compound processing service in the server as described above. The compound processing apparatus provided in this embodiment may, certainly, be provided in various software embodiments, including not limited to various forms of applications, software, software modules, scripts, or code.

FIG. 2 shows the compound processing apparatus 555 stored in the memory 550, which may be software in the form of programs and plug-ins, such as compound processing plug-ins, and includes a series of modules, including an obtaining module 5551, a generation module 5552, a docking module 5553, and a construction module 5554. The obtaining module 5551, the generation module 5552, the docking module 5553, and the construction module 5554 are configured to realize the compound processing function provided in this embodiment.

As previously described, the artificial intelligence-based compound processing method provided in this embodiment may be implemented by various types of electronic devices.

Figure 3A:
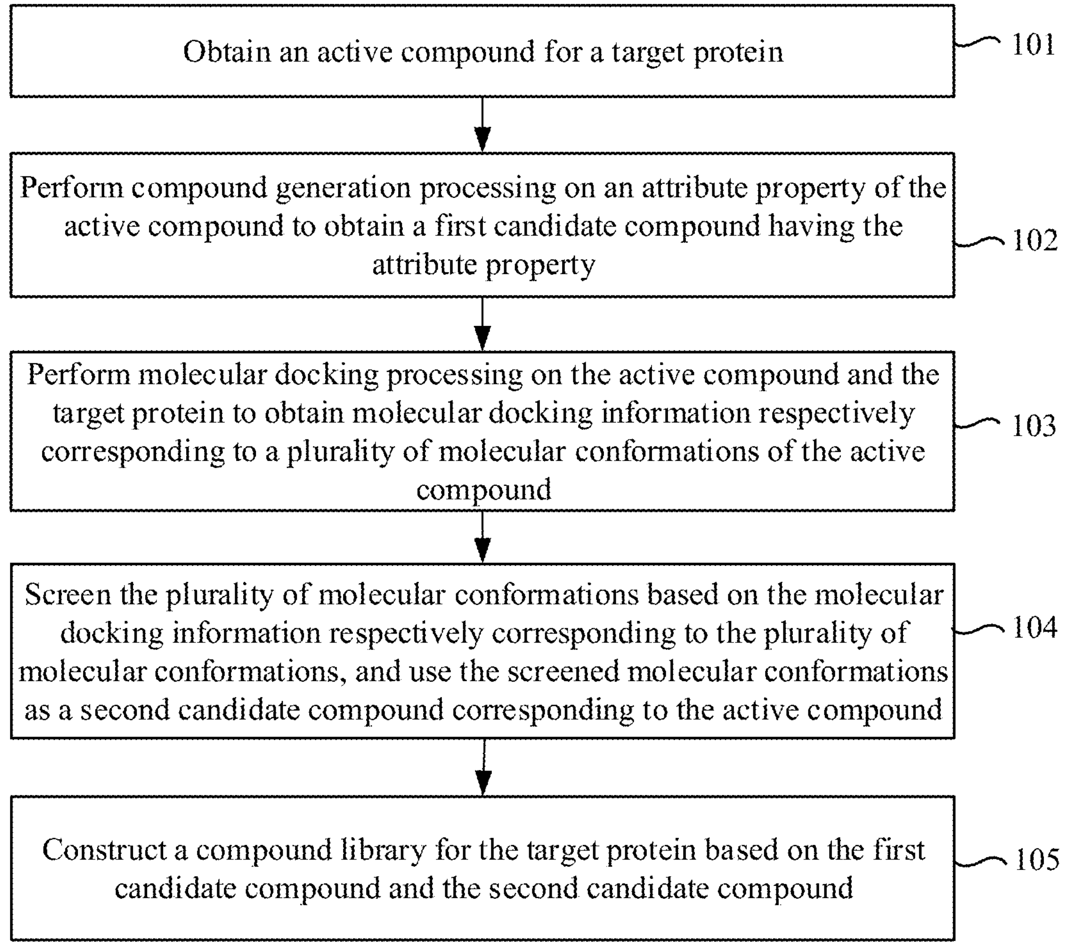
FIGS. 3A-3B are schematic flowcharts of an artificial intelligence-based compound processing method according to an embodiment of this application.

Referring to FIG. 3A, FIG. 3A is a schematic flowchart of an artificial intelligence-based compound processing method according to an embodiment of this application. The flow is described with steps shown in FIG. 3A.

In the following steps, a target protein means a protein having a research value, such as a protein having an effect or influence on a certain disease. An attribute property includes physical properties and chemical properties, namely physicochemical properties of a compound, for example, molecular weight, number of hydrogen bond acceptors, number of hydrogen bond donors, number of rotatable bonds, lipid water partition coefficient, number of specific functional groups, and the like.

In the following steps, a cell state is used for simulating a memory state of neuronal cells in a generation model (namely, historical iteration information of the attribute property), and a hidden state characterizes contextual information of the attribute property.

In step 101, an active compound for a target protein is obtained.

As an example of obtaining a target protein, a user inputs the target protein through an input interface of a terminal, and automatically generates a construction request for a compound library (including the target protein) based on the target protein, and transmits the construction request to a server. The server parses the construction request for the compound library to obtain the target protein. An existing active molecule library is queried based on the target protein, and an active compound for the target protein is queried from the active molecule library.

In step 102, compound generation processing is performed on an attribute property of the active compound to obtain a first candidate compound having the attribute property.

For example, compound generation refers to generation of new molecular structures or modified molecular structures according to desired attributes. Compound generation is based primarily on the splicing or growth of existing molecular fragments in a particular protein pocket to obtain desired molecules. With the rise of deep learning, a generation model based on deep learning may form abstract representation learning (such as molecular representation) on training samples through cascading nonlinear feature transformation, which can effectively extract the basic features of arbitrary input-output relationship, and then generate expected molecules efficiently. For example, the generation model may be a recurrent neural network (RNN), a variational auto encoder (VAE), a generative adversarial network (GAN), or the like.

By way of example, the attribute property of the active compound is obtained, namely the molecular weight, the number of hydrogen bond acceptors, the number of hydrogen bond donors, the number of rotatable bonds, the lipid water partition coefficient, and the number of specific functional groups. The attribute property is inputted to the generation model (such as conditional recurrent neural networks (CRNN)). The generation model performs compound generation processing to obtain inactive compounds (namely, first candidate compound) having the same attribute property and different structures. Since the generation model is trained using a larger data set, the molecules generated by the generation model cover a wider chemical space (more structural diversity), thereby reducing the domain bias of the data set constituted by the first candidate compound. Furthermore, since the generation model is an unsupervised model, the generation model only needs to be trained once and the data set is scalable.

In some embodiments, the operation of performing compound generation processing on an attribute property of the active compound to obtain a first candidate compound having the attribute property includes: encoding the attribute property of the active compound to obtain a state vector of the attribute property; and performing conditional generation processing on the state vector of the attribute property to obtain the first candidate compound having the attribute property.

For example, compound generation processing is performed on the attribute property of the active compound by invoking a generation model to obtain the first candidate compound having the attribute property. The generation model includes at least one first fully-connected layer and at least one second fully-connected layer. The state vector includes a hidden state and a cell state. The operation of encoding the attribute property of the active compound to obtain a state vector of the attribute property includes: encoding the attribute property of the active compound through the first fully-connected layer to obtain the hidden state of the attribute property corresponding to the first fully-connected layer; and encoding the attribute property of the active compound through the second fully-connected layer to obtain the cell state of the attribute property corresponding to the second fully-connected layer.

Figure 4:
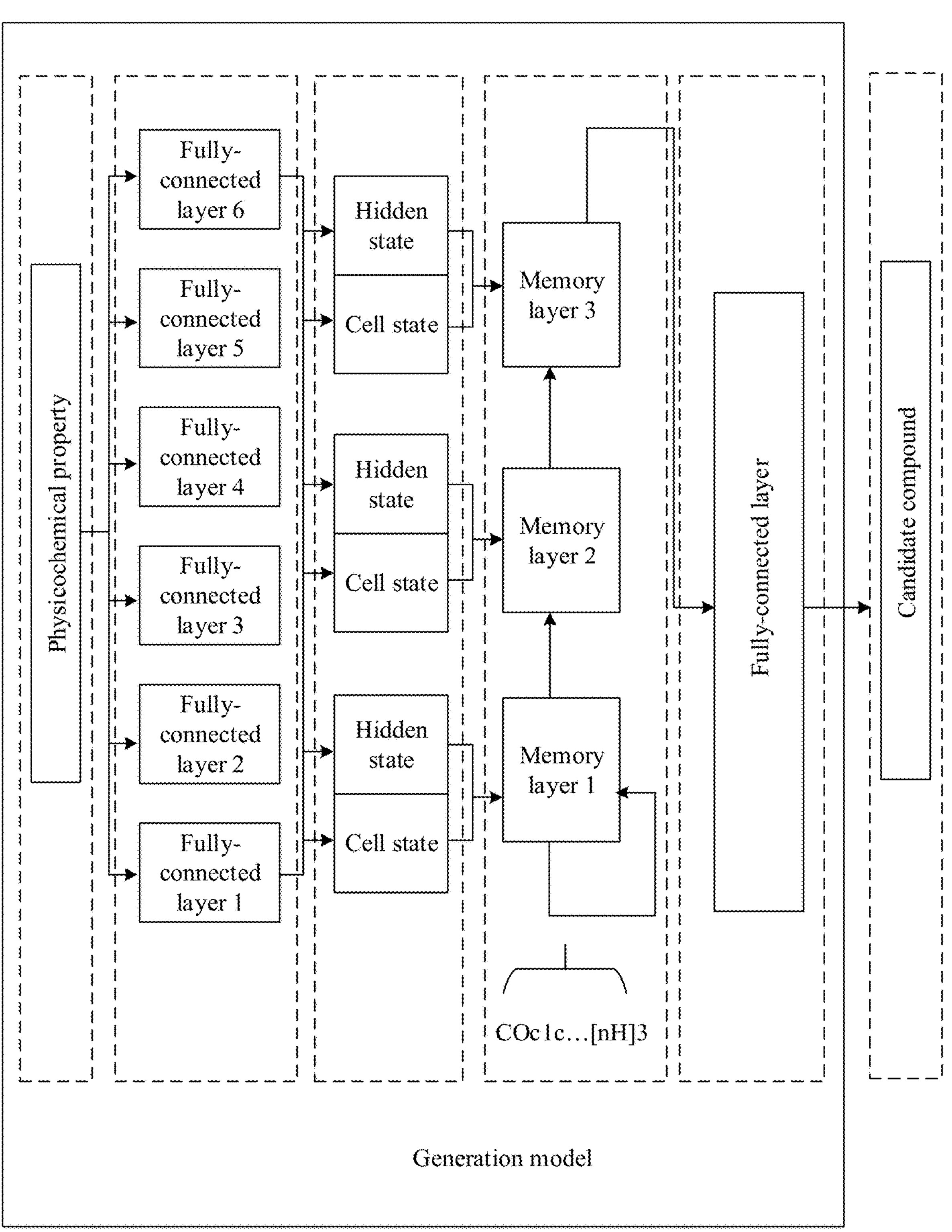
FIG. 4 is a schematic structural diagram of a generation model according to an embodiment of this application.

As shown in FIG. 4, the generation model includes three first fully-connected layers (namely, fully-connected layer 1, fully-connected layer 2, and fully-connected layer 3 shown in FIG. 4) and three second fully-connected layers (namely, fully-connected layer 4, fully-connected layer 5, and fully-connected layer 6 shown in FIG. 4). Model parameters of all the fully-connected layers (including the first fully-connected layers and the second fully-connected layers) are different. The attribute property of the active compound is encoded by fully-connected layer 1 to obtain the hidden state of the attribute property corresponding to fully-connected layer 1. The attribute property of the active compound is encoded by fully-connected layer 2 to obtain the hidden state of the attribute property corresponding to fully-connected layer 2. The attribute property of the active compound is encoded by fully-connected layer 3 to obtain the hidden state of the attribute property corresponding to fully-connected layer 3. The attribute property of the active compound is encoded by fully-connected layer 4 to obtain the cell state of the attribute property corresponding to fully-connected layer 4. The attribute property of the active compound is encoded by fully-connected layer 5 to obtain the cell state of the attribute property corresponding to fully-connected layer 5. The attribute property of the active compound is encoded by fully-connected layer 6 to obtain the cell state of the attribute property corresponding to fully-connected layer 6.

It is to be noted that the encoding processing is carried out by compressing the attribute property (namely, physicochemical properties such as the molecular weight, the number of hydrogen bond acceptors, the number of hydrogen bond donors, the number of rotatable bonds, the lipid water partition coefficient, and the number of specific functional groups) of the active compound through the fully-connected layers in a neural network to compress the attribute property (analog signal) into the hidden state (digital signal) or the cell state (digital signal).

The cell state is used for simulating a memory state of neuronal cells in the generation model (namely, historical iteration information of the attribute property), and the hidden state represents contextual information of the attribute property.

It is to be noted that different state vectors are obtained by encoding the fully-connected layers with different model parameters, so as to subsequently obtain a first candidate compound with the same attribute property and different structures based on various different state vectors. Since the generated first candidate compound covers a wider chemical space (with more structural diversity), the domain bias of a data set composed of the first candidate compound is reduced.

In some embodiments, the operation of encoding the attribute property of the active compound through the first fully-connected layer to obtain the hidden state of the attribute property corresponding to the first fully-connected layer includes: performing the following processing through the first fully-connected layer: performing first vector transformation processing on the attribute property of the active compound to obtain a first transformed vector of the attribute property; and mapping the first transformed vector of the attribute property to obtain the hidden state of the attribute property corresponding to the first fully-connected layer.

For example, first vector transformation processing is performed on the attribute property of the active compound in a vector encoding manner (such as one-hot encoding or a text converter) to obtain the first transformed vector of the attribute property. Then the first transformed vector of the attribute property is mapped through an activation function (such as a Sigmoid function, a Tanh function, or a ReLU function), to obtain the hidden state of the attribute property corresponding to the first fully-connected layer.

It is to be noted that the hidden state of the attribute property can be extracted more accurately by the first vector transformation processing and the mapping processing than by only the mapping processing, whereby compound generation can be performed subsequently based on the accurate hidden state of the attribute property, and the accuracy of a generated compound can be improved.

In some embodiments, the operation of encoding the attribute property of the active compound through the second fully-connected layer to obtain the cell state of the attribute property corresponding to the second fully-connected layer includes: performing the following processing through the second fully-connected layer: performing vector transformation processing on the attribute property of the active compound to obtain a second transformed vector of the attribute property; and mapping the second transformed vector of the attribute property to obtain the cell state of the attribute property corresponding to the second fully-connected layer.

For example, second vector transformation processing is performed on the attribute property of the active compound in a vector encoding manner (such as one-hot encoding or a text converter) to obtain the second transformed vector of the attribute property. Then the second transformed vector of the attribute property is mapped through an activation function (such as a Sigmoid function, a Tanh function, or a ReLU function), to obtain the cell state of the attribute property corresponding to the second fully-connected layer.

It is to be noted that the first vector transformation processing uses different model parameters than the second vector transformation processing. The cell state of the attribute property can be extracted more accurately by the second vector transformation processing and the mapping processing than by only the mapping processing, whereby compound generation can be performed subsequently based on the accurate cell state of the attribute property, and the accuracy of a generated compound can be improved.

In some embodiments, compound generation processing is performed on the attribute property of the active compound by invoking a generation model to obtain the first candidate compound having the attribute property. The generation model includes a plurality of cascaded memory layers. The operation of performing conditional generation processing on the state vector of the attribute property to obtain the first candidate compound having the attribute property includes: performing cascaded decoding processing on the state vector of the attribute property through the plurality of cascaded memory layers to obtain element vectors corresponding to the attribute property; and combining elements corresponding to the element vectors according to a generation order of the element vectors to obtain the first candidate compound having the attribute property.

As shown in FIG. 4, the generation model includes three cascaded memory layers (namely, long short term memory (LSTM)), namely, memory layer 1, memory layer 2, and memory layer 3. Multiple times of cascaded decoding processing are performed by combining memory layer 1, memory layer 2, and the memory layer 3 with respective corresponding state vectors (including the cell state and the hidden state) of the attribute properties to obtain a plurality of element vectors corresponding to the attribute properties. Finally, based on the order of the generated element vectors, elements corresponding to the element vectors are combined so as to obtain the first candidate compound having the attribute property. For example, the first element generated is "C", the second element is "C", . . . , the last element is "H", and then the finally generated candidate compound is "CCC(=O)O . . . H".

It is to be noted that the decoding processing is realized by performing vector transformation on the state vector through the memory layer in the neural network, so as to convert the state vector (one type of digital signal) into an element vector (another type of digital signal). The vector dimensions of the state vector and the element vector may be the same or different. The element vector is used for characterizing an element, and there is a corresponding relationship between the element vector and the element. By combining the state vectors of the corresponding attribute properties of various memory layers through the cascaded decoding processing, the element vector can be obtained more accurately, thereby improving the accuracy of a generated candidate compound.

In some embodiments, the operation of performing cascaded decoding processing on the state vector of the attribute property through the plurality of cascaded memory layers to obtain element vectors corresponding to the attribute property includes: performing the following processing through the plurality of cascaded memory layers: performing cascaded decoding processing on the state vector of the attribute property and a start vector to obtain a first element vector corresponding to the attribute property; and performing cascaded decoding processing on the state vector of the attribute property and an $i^{th}$ element vector to obtain an $i+1^{th}$ element vector corresponding to the attribute property. i is an increasing natural number, $1 \le i \le N$. N is the number of element vectors corresponding to the attribute property.

For example, the process of generating the first element vector is as follows: decoding the state vector of the attribute property corresponding to the first memory layer and the start vector through the first memory layer in the plurality of cascaded memory layers; outputting a decoding result of the first memory layer to a memory layer cascaded thereto, and continuing to perform decoding processing and decoding result output through the memory layer cascaded thereto, until a decoding result is outputted to the last memory layer; and mapping a decoding result outputted by the last memory layer to obtain the first element vector corresponding to the attribute property. It is to be noted that the start vector is used for identifying the start of decoding, and may be a null vector, a start character (for example, "^"), or an all-zero vector.

For example, the process of generating the $i+1^{th}$ element vector is as follows: decoding the state vector of the attribute property corresponding to the first memory layer and the $i^{th}$ element vector through the first memory layer in the plurality of cascaded memory layers; outputting a decoding result of the first memory layer to a memory layer cascaded thereto, and continuing to perform decoding processing and decoding result output through the memory layer cascaded thereto, until a decoding result is outputted to the last memory layer; and mapping a decoding result outputted by the last memory layer to obtain the $i+1^{th}$ element vector corresponding to the attribute property.

In some embodiments, the operation of continuing to perform decoding processing and decoding result output through the memory layer cascaded thereto includes: decoding, through a $j^{th}$ memory layer in the plurality of cascaded memory layers, the state vector of the attribute property corresponding to the $j^{th}$ memory layer and a decoding result outputted by a $j-1^{th}$ memory layer to obtain a decoding result of the $j^{th}$ memory layer; and outputting the decoding result of the $j^{th}$ memory layer to a decoding result of a $j+1^{th}$ memory layer. j is an increasing natural number, $1<j<M$. M is the number of the memory layers.

As shown in FIG. 4, memory layer 1 (namely, the first memory layer) decodes the state vector and the start character "^" (start vector) inputted from the fully-connected layer to memory layer 1 to obtain a decoding result of memory layer 1 (new state vector corresponding to memory layer 1), and the decoding result of memory layer 1 is outputted to memory layer 2 (namely, the second memory layer). Memory layer 2 decodes the state vector of the attribute property inputted from the fully-connected layer to memory layer 2 and the decoding result outputted by memory layer 1 to obtain a decoding result of memory layer 2 (new state vector corresponding to memory layer 2), and the decoding result of memory layer 2 is outputted to memory layer 3 (namely, the third memory layer). Memory layer 3 decodes the state vector of the attribute property inputted from the fully-connected layer to memory layer 3 and the decoding result outputted by memory layer 2 to obtain a decoding result of memory layer 3 (new state vector corresponding to memory layer 3), the decoding result of memory layer 3 is mapped to obtain a probability distribution of one candidate element vector corresponding to the attribute property, and the candidate element vector corresponding to the maximum probability in the probability distribution is used as the first element vector corresponding to the attribute property.

In some embodiments, the operation of decoding the state vector of the attribute property corresponding to the $j^{th}$ memory layer and a decoding result outputted by a $j-1^{th}$ memory layer to obtain a decoding result of the $j^{th}$ memory layer includes: performing forget gate-based forget processing on the cell state of the attribute property corresponding to the $j^{th}$ memory layer, the hidden state of the attribute property, and the decoding result outputted by the $j-1^{th}$ memory layer, to obtain a forget vector of the $j^{th}$ memory layer; performing update gate-based memory update processing on the forget vector of the $j^{th}$ memory layer, the hidden state of the attribute property, and the decoding result outputted by the $j-1^{th}$ memory layer, to obtain the updated cell state corresponding to the $j^{th}$ memory layer; and mapping the hidden state of the attribute property, the decoding result outputted by the $j-1^{th}$ memory layer, and the updated cell state to obtain the decoding result of the $j^{th}$ memory layer.

For example, the memory layer can solve the long dependency problem, and the robustness of the element vector is improved by solving the long dependency problem of the state vector through the memory layer. The memory layer simulates the memory state of a neuronal cell with the cell state, and three gates (including a forget gate, an update gate, and an output gate) are designed for the neuronal cell to control the neuronal cell. For example, for the $j^{th}$ memory layer, the forget gate-based forget processing is shown in Formulas (1)-(2):

$$\tau_{forget} = \text{Sigmoid}(W_f[H^{t-1}, X^t] + b_f) \tag{1}$$

$$C^{t-1}_{forget} = C^{t-1} \times \tau_{forget} \tag{2}$$

where $H^{t-1}$ represents the hidden state of the attribute property corresponding to the $j^{th}$ memory layer; $X^t$ represents the decoding result outputted by the $j-1^{th}$ memory layer; $C^{t-1}$ represents the cell state of the attribute property corresponding to the $j^{th}$ memory layer;

$$C^{t-1}_{forget}$$

represents the forget vector of the $j^{th}$ memory layer; $W_f$ represents a learnable parameter of the forget gate; $b_f$ represents a bias parameter of the forget gate; and t represents a $t^{th}$ element generated.

For example, for the $j^{th}$ memory layer, the update gate-based memory update processing is shown in Formulas (3)-(5):

$$\tau_{update} = \text{Sigmoid}(W_u[H^{t-1}, X^t] + b_u) \tag{3}$$

$$C^t_{update} = \text{Tanh}(W_c[H^{t-1}, X^t] + b_c) \tag{4}$$

$$C^t = C^{t-1}_{forget} + C^t_{update} \times \tau_{update} \tag{5}$$

where $W_u$ and $W_c$ represent learnable parameters of the update gate, $b_c$ represents bias of the update gate, and $C^t$ represents the updated cell state corresponding to the $j^{th}$ memory layer, which is used as the cell state of the attribute property corresponding to the $j^{th}$ memory layer during the generation of a next element.

For example, for the $j^{th}$ memory layer, the output gate-based mapping processing is shown in Formulas (6)-(7):

$$\tau_{output} = \text{Sigmoid}(W_o[H^{t-1}, X^t] + b_o) \tag{6}$$

$$H^t = \text{Tanh}(C^t) \times \tau_{output} \tag{7}$$

where $W_o$ represents a learnable parameter of the output gate, $b_o$ represents bias of the output gate, and $H^t$ represents the mapped hidden state corresponding to the $j^{th}$ memory layer (namely, the decoding result of the $j^{th}$ memory layer), which is used as the hidden state of the attribute property corresponding to the $j^{th}$ memory layer during the generation of a next element.

In some embodiments, the operation of performing cascaded decoding processing on the state vector of the attribute property and an $i^{th}$ element vector to obtain an $i+1^{th}$ element vector corresponding to the attribute property includes: decoding the updated cell state corresponding to the first memory layer, the mapped hidden state corresponding to the first memory layer, and the $i^{th}$ element vector through the first memory layer in the plurality of cascaded memory layers; outputting a decoding result of the first memory layer to a memory layer cascaded thereto, and continuing to perform decoding processing and decoding result output through the memory layer cascaded thereto, until a decoding result is outputted to the last memory layer; and mapping a decoding result outputted by the last memory layer to obtain the $i+1^{th}$ element vector corresponding to the attribute property.

For example, after the first element vector is generated, the first element vector is inputted to the first memory layer, and the foregoing cascaded decoding processing is iterated. By means of the first memory layer, the updated cell state corresponding to the first memory layer (namely, the updated cell state of the first memory layer during the generation of the $i^{th}$ element vector), the mapped hidden state corresponding to the first memory layer (namely, the mapped hidden state of the first memory layer during the generation of the $i^{th}$ element vector), and the $i^{th}$ element vector are decoded to obtain the decoding result of the first memory layer. The decoding result of the first memory layer is outputted to a memory layer cascaded thereto. By means of the $j^{th}$ memory layer in the plurality of cascaded memory layers, the state vector of the attribute property corresponding to the $j^{th}$ memory layer (including the updated cell state corresponding to the $j^{th}$ memory layer and the mapped cell state corresponding to the $j^{th}$ memory layer) and the decoding result outputted by the $j-1^{th}$ memory layer are decoded to obtain the decoding result of the $j^{th}$ memory layer, and the decoding result of the $j^{th}$ memory layer is outputted to the decoding result of the $j+1^{th}$ memory layer, where j is an increasing natural number, $1<j<M$, and M is the number of the memory layers. The decoding result is outputted to the last memory layer, and the decoding result outputted by the last memory layer is mapped to obtain the $i+1^{th}$ element vector corresponding to the attribute property.

In step 103, molecular docking processing is performed on the active compound and the target protein to obtain molecular docking information respectively corresponding to a plurality of molecular conformations of the active compound.

For example, molecular docking processing is performed on the active compound and the target protein to obtain a molecular docking score (namely, molecular docking information) of each molecular conformation. A second candidate compound is obtained subsequently by screening based on the molecular docking score of the molecular conformation. Finally, a compound library for a target protein is constructed based on the generated first candidate compound with different structures and the second candidate compound screened by molecular docking. The compound library constructed by combining the two candidate compounds can alleviate a noncausal bias relative to the compound library constructed by only one candidate compound (for example, the first candidate compound or the second candidate compound).

The molecular docking is a process in which molecules undergo geometric matching and energy matching in protein pockets, and includes two stages, namely conformation search and scoring function evaluation. The conformation search refers to changing the conformations of molecules by changing three-dimensional space coordinates of the molecules and dihedral angles between atoms. The scoring function evaluation is to use a scoring function to predict the binding affinity between specific protein ligand binding conformations.

In some embodiments, the operation of performing molecular docking processing on the active compound and the target protein to obtain molecular docking information respectively corresponding to a plurality of molecular conformations of the active compound includes: performing molecular dynamics simulation processing based on the target protein to obtain a binding pocket of the target protein; structurally adjusting the target protein to obtain the adjusted target protein; and docking the adjusted target protein to the binding pocket of the target protein to obtain the molecular docking information respectively corresponding to the plurality of molecular conformations of the active compound.

For example, the target protein is structurally adjusted to obtain the adjusted target protein. The adjusted target protein (namely, the molecular conformation) is docked to the binding pocket of the target protein using a FTMap method (a molecular docking method), to obtain the molecular docking score of the molecular conformation (namely, using a scoring function to predict the binding affinity between the target protein and the molecular conformation).

In some embodiments, the operation of structurally adjusting the target protein to obtain the adjusted target protein includes: repairing side chains and ring structures in the target protein to obtain the repaired target protein; adjusting bond orders and formal charges of the repaired target protein to obtain the adjusted target protein; and performing force field optimization processing on the direction of hydrogen atoms of the adjusted target protein to obtain the adjusted target protein.

For example, the structure adjustment process is as follows: (1) repairing the target protein structure by deleting hydrogen in the target protein and re-adding hydrogen, forming necessary bonds with proximal sulfur, and filling the missing side chains and the missing ring structures of the target protein (namely, repair processing); (2) adjusting the bond orders and the formal charges in the target protein (namely, adjustment processing); and (3) adjusting the direction of hydrogen atoms in the target protein to make a hydrogen bond network more stable, and performing force field optimization on the whole molecular structure (namely, force field optimization processing).

In some embodiments, the process of obtaining a plurality of molecular conformations of the active compound during molecular docking is as follows: performing format conversion processing on the active compound to obtain a converted format of the active compound; constructing a three-dimensional conformation of the active compound based on the converted format of the active compound; determining a position where a hydrogen atom can be added based on the three-dimensional conformation of the active compound; and adding the hydrogen atom to the position where the hydrogen atom can be added, to obtain the molecular conformation of the active compound.

For example, the active compound is converted from an SMILES format to PDB, MOL2, PDBQT, and SDF formats. Then, the three-dimensional conformation of the active compound is simulated by a molecular design application (for example, Schrödinger) in conjunction with the converted format of the active compound, and a position (a basic position) where a hydrogen atom can be added to the active compound is determined based on the three-dimensional conformation of the active compound, and the hydrogen atom is added to the hydrogen atom-added position, so as to obtain the molecular conformation of the active compound.

In step 104, the plurality of molecular conformations are screened based on the molecular docking information respectively corresponding to the plurality of molecular conformations, and the screened molecular conformations are used as a second candidate compound corresponding to the active compound.

For example, after obtaining the molecular docking information of each molecular conformation, when the molecular docking information of the molecular conformation is less than a score threshold (for example, −4), the molecular conformation is used as the second candidate compound corresponding to the active compound. Alternatively, after obtaining the molecular docking information of each molecular conformation, the plurality of molecular conformations are ranked in an ascending order based on the molecular docking information of each molecular conformation, and a part of the molecular conformations top-ranked in the ascending order result are used as the second candidate compound corresponding to the active compound.

In step 105, a compound library for the target protein is constructed based on the first candidate compound and the second candidate compound.

For example, after obtaining the first candidate compound and the second candidate compound, the first candidate compound and the second candidate compound are used as compounds for compound screening in the compound library for the target protein. The compound library constructed by candidate compounds obtained by two methods can alleviate the causal bias.

Figure 3B:
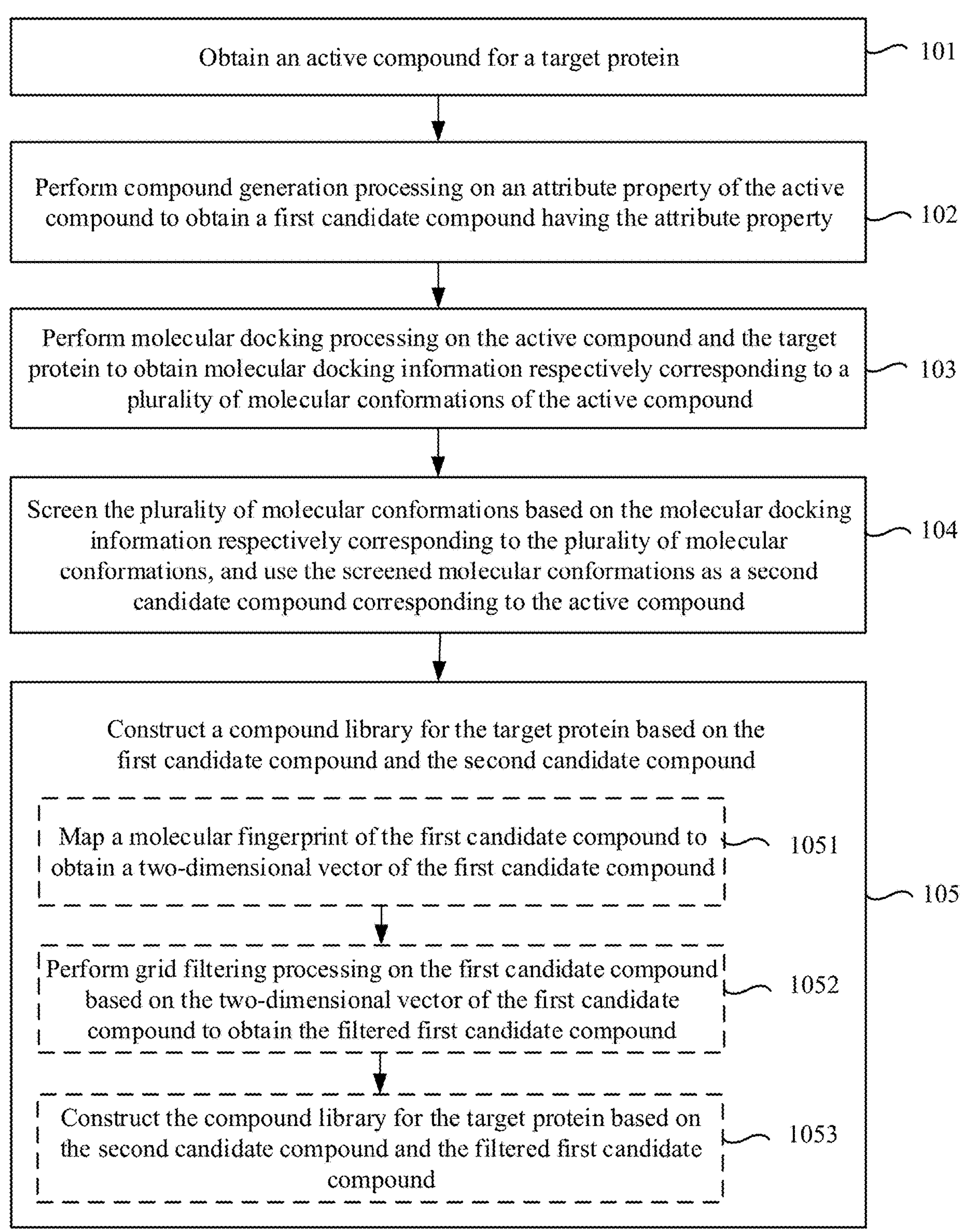

Referring to FIG. 3B, FIG. 3B is a schematic flowchart of an artificial intelligence-based compound processing method according to an embodiment of this application. In FIG. 3B, step 105 in FIG. 3A may be implemented by step 1051 to step 1053. In step 1051, a molecular fingerprint of the first candidate compound is mapped to obtain a two-dimensional vector of the first candidate compound. In step 1052, grid filtering processing is performed on the first candidate compound based on the two-dimensional vector of the first candidate compound to obtain the filtered first candidate compound. In step 1053, the compound library for the target protein is constructed based on the second candidate compound and the filtered first candidate compound.

For example, the grid filtering process is as follows: constructing a two-dimensional chemical space having a plurality of grids based on the two-dimensional vector of the first candidate compound; mapping the first candidate compound to the two-dimensional chemical space; and filtering the first candidate compound in the two-dimensional chemical space based on an accommodation space of each of the grids to obtain the filtered first candidate compound.

Figure 5:
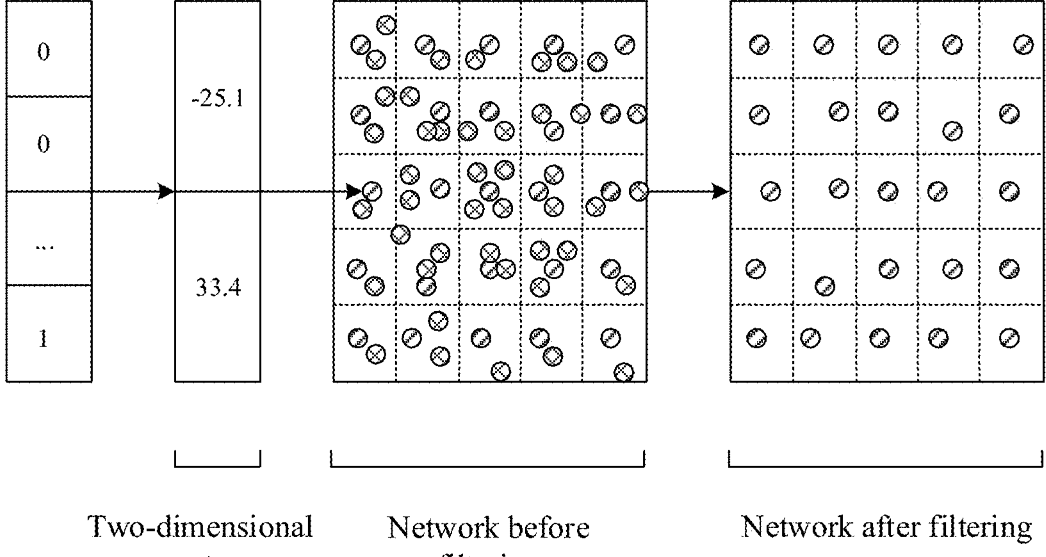
FIG. 5 is a schematic diagram of grid filtering according to an embodiment of this application.

As shown in FIG. 5, grid filtering is used to delete compounds with high structural similarity among the first candidate compounds. A molecular fingerprint is first calculated for each first candidate compound generated. The molecular fingerprint is then non-linearly mapped to the two-dimensional chemical space to obtain a two-dimensional vector, so as to visualize the distribution of all the first candidate compounds in the chemical space. Based on the two-dimensional vector, a minimum value and a maximum value are calculated for each dimension, and the vector is divided into a plurality of intervals based on the minimum value and the maximum value of each dimension. One interval of each dimension forms a grid in the whole two-dimensional chemical space. A plurality of generated first candidate compounds are mapped into the grid in the two-dimensional chemical space. When the accommodation space of each grid is 1, each grid retains one first candidate compound, so as to discard compounds with a similar topology structure in the grid, thereby improving the diversity of the filtered first candidate compounds.

An application of the embodiments of this application in an actual application scenario will be described below.

The data set in the related art has the following problems. In the data set based on decoys, 42% of active molecules in a DUD data set have net charges, while only 15% of decoys have net charges. This difference in the distribution of physicochemical properties results in that a machine learning algorithm can easily classify active compounds from inactive compounds according to the net charges, resulting in the bias of artificial enrichment. The active molecules in the DUDE and DEKOIS data sets and the decoys are defined according to the differences in the topological structures and pharmacophore information, respectively. This single difference will cause the machine learning algorithm to classify compounds according to the structural similarity and pharmacophore similarity, resulting in the noncausal bias.

Although the data sets based on real experimental data, such as LIT-PCBA and MUV, are unbiased so that there is no obvious difference in chemical structures and pharmacophore information between the active molecules and the decoys, there are some problems in these data sets, such as extreme imbalance in the number of positive and negative samples, low scalability, and domain bias caused by a single chemical structure.

To solve the foregoing problems, an embodiment of this application proposes an artificial intelligence-based compound processing method (APCB). A conditional recurrent neural network (CRNN) is trained on a large data set to construct a generation model. The CRNN may generate compounds with large probability that are structurally dissimilar and of similar physicochemical properties. Since the CRNN is trained using a larger data set, molecules generated by the CRNN cover a wider chemical space (more structural diversity), thereby reducing the domain bias of the data set. Furthermore, since the CRNN is an unsupervised generation model, the generation model only needs to be trained once and the data set is scalable. In addition to decoys matching based on physicochemical properties, low-scored conformations of active molecules are introduced as decoys. By mixing two types of decoys, two noncausal biases are introduced to counteract the influence on the machine learning algorithm, thus forcing the machine learning algorithm to learn a protein-ligand interaction mode from the data set. Furthermore, a method for eliminating the analogue bias of a data set by calculating a molecular fingerprint, reducing the dimensions of the molecular fingerprint to two dimensions, and performing grid filtering is adopted.

A non-hidden-bias and scalable data set is constructed in this embodiment, and an AI-based scoring function is constructed and evaluated based on the non-hidden-bias and scalable data set, to perform accurate virtual screening through the constructed scoring function.

The CRNN is used to generate decoys matching with physicochemical properties according to existing active compounds for a specific target (namely, a target protein) in this embodiment, and docking software is used to generate decoys conformations with a lower score. A target number of required decoys is determined according to the existing number of active compounds and an appropriate positive and negative sample proportion. Extended connectivity fingerprints (ECFP) of the data set are calculated, the dimensions are reduced to two dimensions by a non-linear dimension reduction algorithm (such as T-SNE algorithm), and the target number of decoys is obtained by adjusting the grid number and performing grid filtering. Finally the active compounds and the decoys are combined to form a data set, which is further divided into a training set, a validation set and a test set for AI modeling. The positive and negative sample proportion is adjusted by adjusting the number of decoys generated, and a corresponding benchmark is customized to validate and compare the performances of the AI scoring function.

The generation model in this embodiment is described in detail as follows.

Figure 6:
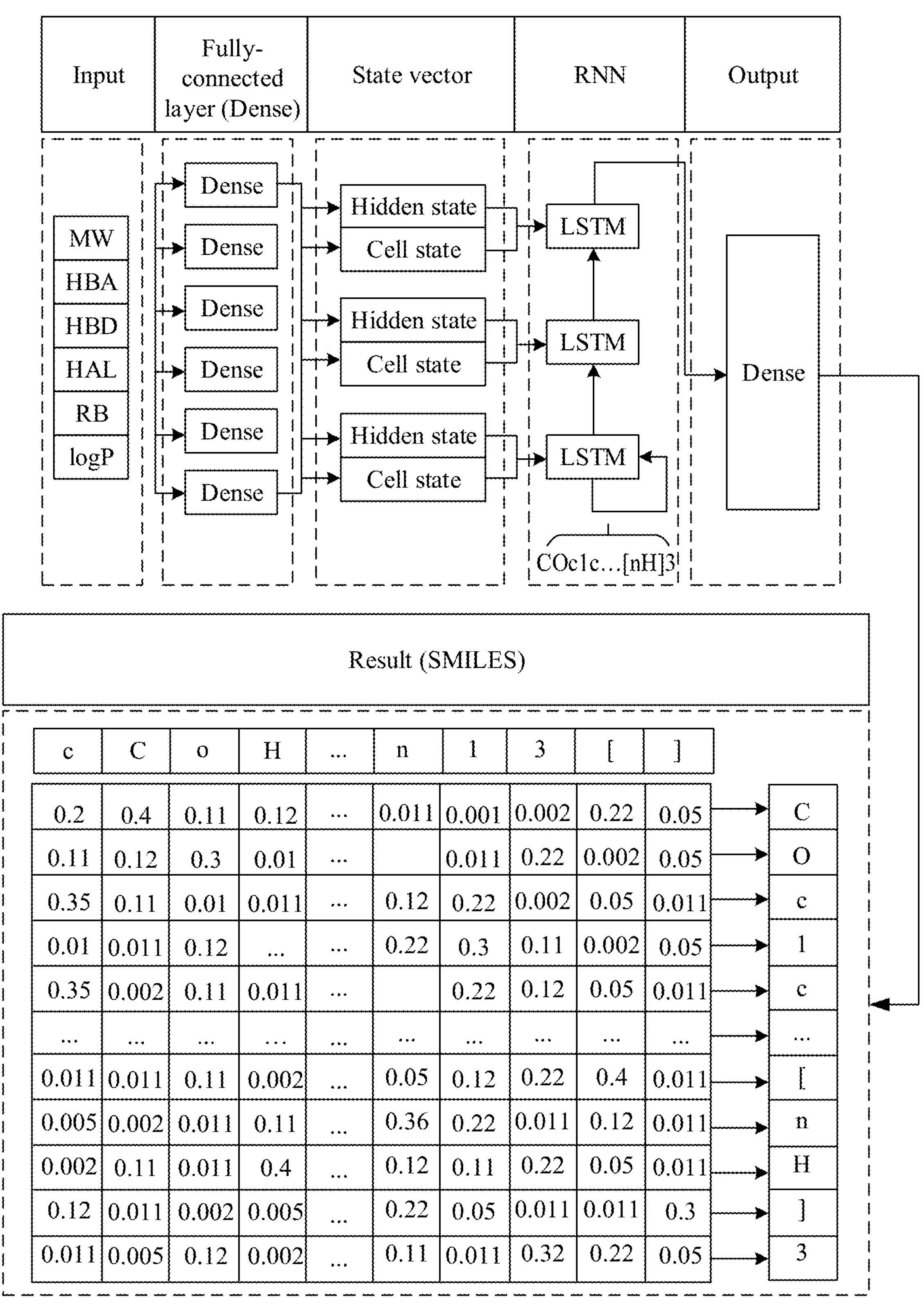
FIG. 6 is a schematic structural diagram of a generation model according to an embodiment of this application.

The generation model in this embodiment is a conditional recurrent neural network, and other conditional generation models, such as a conditional variational auto encoder (CVAE), may also be used in practice. Taking the CRNN as an example, the network architecture is as shown in FIG. 6. A data set used by a construction model is ChEMBL2516. The training set (1347173 molecules) and the test set (149679 molecules) are divided in a proportion of 9:1.

The generation model (for example, CRNN) is trained as follows.

(1) A molecular vocabulary ('$^Brc1(−23[nH])45C=NOso#FlS67+89%0') is established. "^" is used as a start token, "$" is used as an end token, and "?" is used as an unknown token. The start token "^" is added to the start of the compound SMILES as an input sequence, the end token "$" is added to the end of the compound SMILES as a target sequence, and all compound sequences (including the input sequence and the target sequence) are filled to 128 characters with the unknown token.

Taking CCC(═O)O as an example, the input sequence is "^CCC(═O)O?? . . . ?", the target sequence is "CCC(═O)OS? ?", and the length of all the sequences is 128.

(2) Six physicochemical properties (MW, HBA, HBD, RB, Log P, and HAL) of each compound are calculated. The physicochemical properties are inputted into the CRNN to obtain hidden variables as initial state vectors (including a cell state and a hidden state) through six 256-dimensional fully-connected layers (for example, long short term memory (LSTM) layers) adopting the ReLU activation function respectively.

(3) The input sequence is one-hot encoded, the encoded vectors are inputted to the LSTM layers in a sequence order, and the vectors are outputted in sequence after passing through the three LSTM layers. The output vector is inputted into a fully-connected layer adopting the activation function softmax, and an element vector of sequence length*vocabulary dimension is finally obtained.

During the training process of this generation model, characters (namely, elements) corresponding to the input and output of the CRNN may be misaligned. Taking CCC(═O)O as an example, the first character start token "A" (namely, a start character) of the input sequence is used as the input, and the first character "C" of the target sequence is used as the output. The second character "C" of the input sequence is used as the input, and the second character "C" of the target sequence is used as the output. By analogy, the last valid character "O" of the input sequence is used as the input, and the last valid character (the end token "$") of the target sequence is used as the output.

A teacher forcing method is used in this embodiment. A $t-1^{th}$ real character instead of a CRNN predicted character is used as the input when calculating a $t^{th}$ output character. Taking CCC(═O)O as an example, in the complete training process of the CRNN, the LSTM first receives the start token "^" of the input sequence, and outputs a predicted next character as "0" (a character predicted incorrectly, and a character predicted correctly is "C") after calculation. If the teacher forcing method is not used, "O" is used as the input of the LSTM during training. In this way, errors will be introduced into the subsequent sequence prediction. If the teacher forcing method is used, the correct "C" is used as the input of the LSTM to help the model converge faster.

(4) The target sequence is one-hot encoded to obtain a target vector (Ground Truth), the loss of the CRNN is calculated based on a vector outputted by the CRNN and a cross entropy loss function of the target vector, and an optimizer (such as Adam) is used for gradient descent to update parameters. During the training, a batch size is 128, the number of training rounds (Epoch) is 100, and a learning rate is $10^{-3}$ in the first 50 rounds and evenly reduced to $10^{-6}$ in the last 50 rounds.

After the generation model is trained by the foregoing training, the generation model is applied to generate a compound, so as to construct a database. The application process of the generation model is as follows.

(1) The physicochemical properties of index molecules are calculated and used as the input of the CRNN, and the corresponding state vectors (hidden state and cell state) are calculated by the CRNN according to the inputted physicochemical properties and transferred to the LSTM layer.

(2) The LSTM layer receives the state vector and the start token "^", outputs a next character and updates the state vector until the outputted character is the end token "$".

The LSTM layer simulates the memory state of a neuronal cell with the cell state, and three gates (a forget gate, an update gate, and an output gate) are designed for the neuronal cell to control the neuronal cell. The LSTM layer receives the cell state $C^{t-1}$ during the generation of the previous character, the hidden state $H^{t-1}$, and the input $X^t$ of the current LSTM layer, and selects to forget part of the historical memory (forgetting the historical cell state $C^{t-1}$) through the forget gate. The calculation process of the forget gate is as follows:

$$\tau_{forget} = \text{Sigmoid}\left(W_f\left[H^{t-1}, X^t\right] + b_f\right), C^{t-1}_{forget} = C^{t-1} \times \tau_{forget}.$$

The short term memory is updated (the short term memory is calculated and updated based on the historical hidden state $H^{t-1}$ and the input $X^t$ of the current LSTM layer) through the update gate. The calculation process of the update gate is as follows: $\tau_{update}$=Sigmoid($W_u[H^{t-1}, X^t]+b_u$), $$C^t_{update} = \mathrm{Tanh}(W_c[H^{t-1}, X^t] + b_c),$$

$$C^t = C^{t-1}_{forget} + C^t_{update} \times \tau_{update}.$$

The hidden variable $H^t$ of the current cell is output by integrating the historical memory and the short term memory through the output gate. The calculation process of the output gate is as follows: $\tau_{output}$=Sigmoid($W_o[H^{t-1}, X^t]b_o$) $H^t$=Tanh($C^t$)×$\tau_{output}$.

The current LSTM layer outputs a next character based on the state vector ($H^{t-1}$, $C^{t-1}$) and $X^t$, and updates the state vector into $H^t$, $C^t$. The foregoing calculation processes are iterated until the outputted character is the end token "$".

(3) The element vector outputted by the model takes the maximum value in the vocabulary and indexes the position of the vocabulary to obtain corresponding elements, so as to obtain the generated molecule SMILES.

The molecular docking process in this embodiment is described in detail as follows.

Low-scored conformations are generated by a Glide module in molecular design software Schrödinger. A PDB file for the target protein is first prepared by using a protein prepare wizard from Schrödinger. The processing is as follows: removing unnecessary moisture from the environment; repairing the target protein structure by deleting hydrogen and re-adding hydrogen, forming necessary bonds with proximal sulfur, and filling the missing side chains and the missing rings; adjusting the bond orders and the formal charges; calculating, by PROPKA, a protonation state of protein residues with PH of 7.0, and generating an ionization state of non-protein atoms through Epik; and adjusting the direction of hydrogen atoms to make a hydrogen bond network more stable, and performing force field optimization on the whole target protein structure.

Also, LigPrep of Schrödinger is used to correct hydrogen to generate an appropriate conformation for each active compound.

After preparation of the target protein and ligand, a co-crystal ligand in the original target protein PDB file is extracted and used to locate a binding site and generate a grid file required for Glide docking. All prepared active compounds are docked to a target protein pocket (the molecular conformation is searched and scored with the scoring function), and 200 conformations are retained for each active compound. The scores of positive and negative samples are observed, and an appropriate docking score (for example, −4) is selected as a threshold for further conformation filtering. When the docking score for a conformation of an active compound is less than the threshold, the conformation of the active compound is retained.

The grid filtering process in this embodiment is described in detail as follows.

To eliminate the analogue bias, it is critical to select compounds that are evenly distributed across a structural chemical space (that is, using the CRNN to generate decoys matching with physicochemical properties, namely, PCB). Here, grid filtering is used to delete compounds with high structural similarity.

Figure 7:
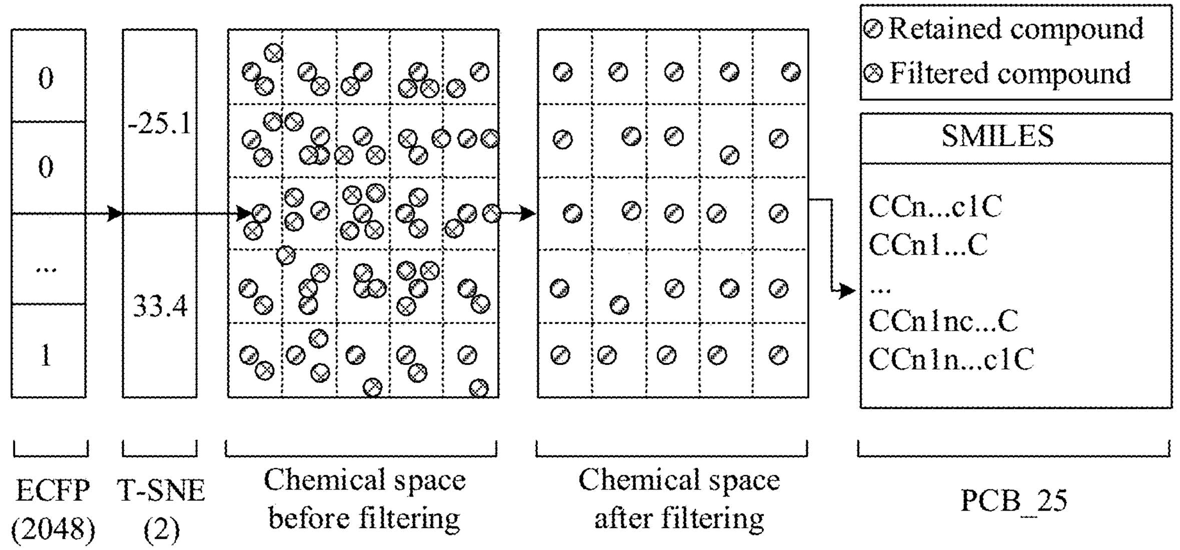
FIG. 7 is a schematic diagram of grid filtering according to an embodiment of this application.

As shown in FIG. 7, the ECFP of the compounds is first calculated. A T-SNE algorithm is then used to non-linearly map a 2048-dimensional ECFP to a two-dimensional vector, so as to visualize the distribution of the compounds in the chemical space. Based on the two-dimensional vector, the minimum and maximum values are calculated for each dimension, and a fixed step size is set, so as to divide the vector into different intervals. One interval in each dimension forms a grid in the whole two-dimensional chemical space, one compound is retained for each grid, and topologically similar compounds are discarded. The interval step size is a super-parameter, which may be adjusted according to requirements. PCB 25 in FIG. 7 represents a PCB data set obtained by 25 grid filters.

In order to validate that the data set constructed in this embodiment has no hidden bias, this embodiment of this application is subjected to the following validation tests:

In this embodiment, LIT-PCBA is used as a control for two reasons. (1) LIT-PCBA is an unbiased data set designed for machine learning and virtual screening, which is also the final goal. (2) The compounds in LIT-PCBA have experimental data, thereby avoiding the possibility of decoys introducing false negatives.

An APCB data set is generated first based on the active compound in LIT-PCBA (target: ALDH1 and MAPK1). Various hidden biases, including artificial enrichment, analogue bias, domain bias, and noncausal bias, are then validated. The machine learning model used in the validation process includes an improved gradient boost algorithm (XGBoost model) and a graph neural network model (IGN). The results show that the artificial enrichment, the analogue bias, and the noncausal bias constructed in this embodiment are equivalent to those of LIT-PCBA without the hidden bias, while the domain bias is lower than that of LIT-PCBA. Moreover, the scalability and customizability of the data set constructed in this embodiment are superior to LIT-PCBA.

The manual enrichment validation is as follows.

For ALDH1 and MAPK1, the CRNN is used to generate decoys according to active compounds in this embodiment, and the decays are further filtered according to the physicochemical properties of the decoys so as to remove artificial enrichment.

Figure 8:
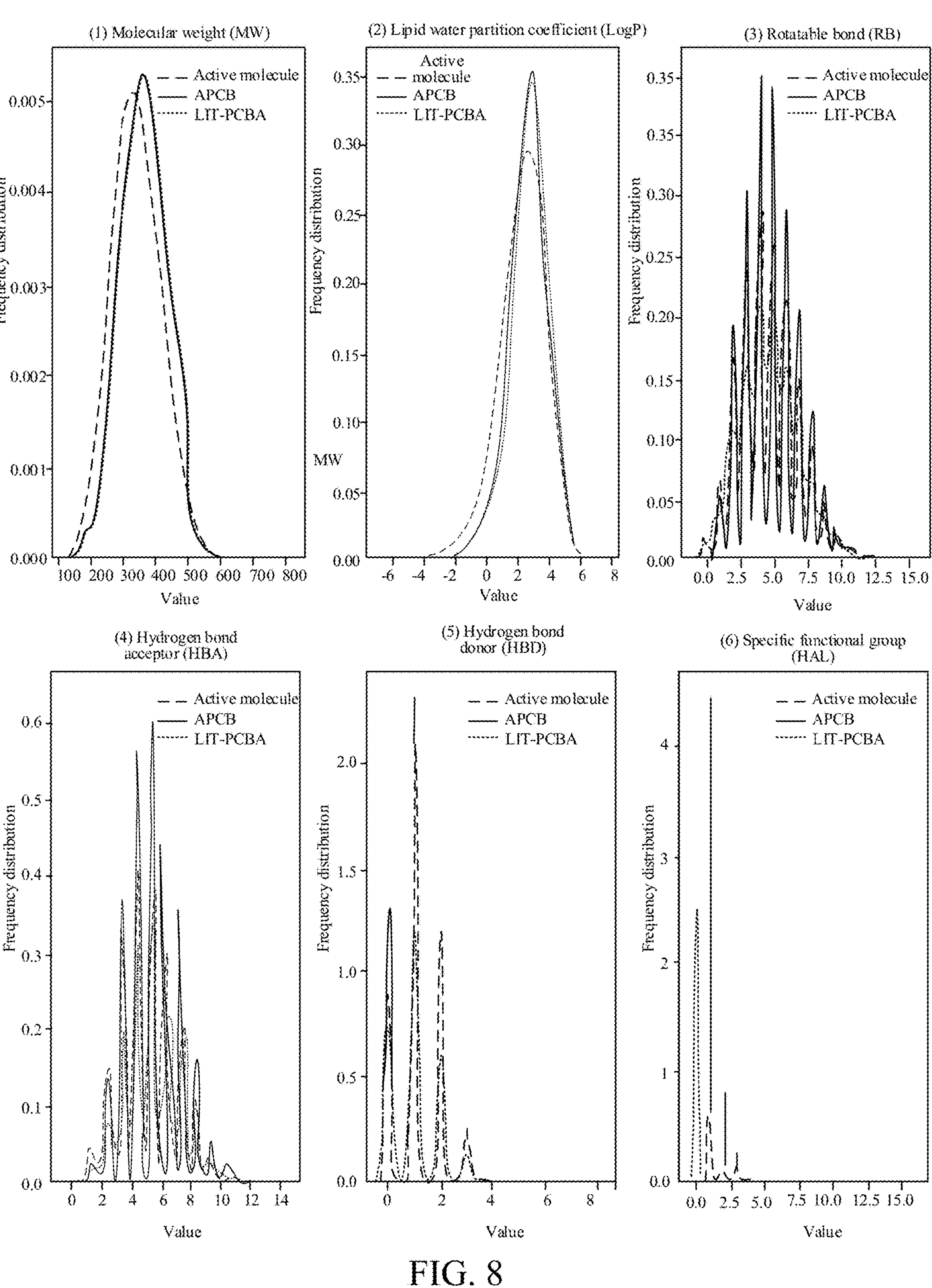
FIG. 8 is a distribution diagram of physicochemical properties of a data set according to an embodiment of this application.

As shown in FIG. 8, the distribution of the decoys (inactive compounds) in APCB and LIT-PCBA is similar to that of the active compounds. More specifically, the decoys of APCB show almost the same distribution as active ingredients in terms of MW and Log P. In terms of HBD and HAL, APCB is closer to the distribution of the active ingredients than the decoys in LIT-PCBA. LIT-PCBA has performed better than APCB in RB and HBA. In fact, the criteria for physicochemical property screening can be increased to further reduce artificial enrichment, and since CRNN may generate compounds continuously, there is no need to worry about the number of compounds, which is not possible with data sets based on real data and decoys.

The validation of the analogue bias and the domain bias is as follows.

In order to explore the analogue bias caused by structural similarities existing in APCB data set, different grid numbers are used for grid filtering to generate the APCB data sets of different sizes in this embodiment.

The APCB data set includes 50 decoys conformations and 50 decoys matching with the physicochemical properties of each active compound. A total positive and negative sample proportion is 1:100. Furthermore, the original APCB data set is transferred to grid filters with grid numbers of 90000 and 1000000, respectively, so as to obtain an APCB 9 W data set and an APCB 100 W data set. The grid number of 90000 is selected in order to make the data sizes of APCB and LIT-PCBA similar, while the grid number of 1000000 is selected for grid filtering in order to obtain a data set with a higher number of ligands, thereby facilitating deep learning training.

Figure 9A:
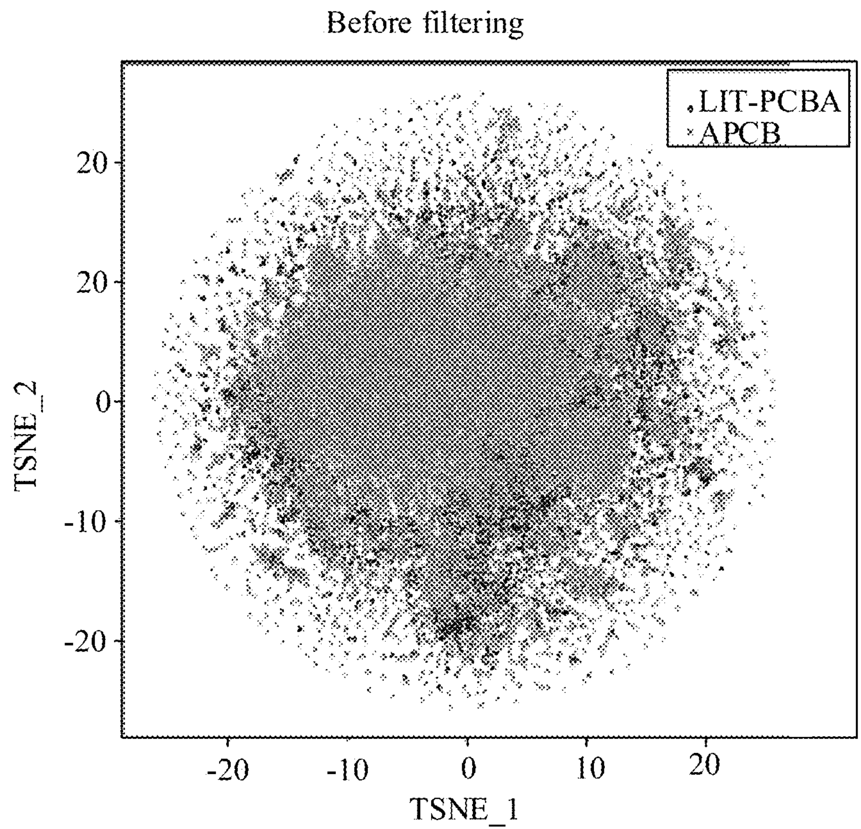
FIG. 9A is a schematic diagram of a chemical structure space of APCB and LIT-PCBA before grid filtering according to an embodiment of this application.
Figure 9B:
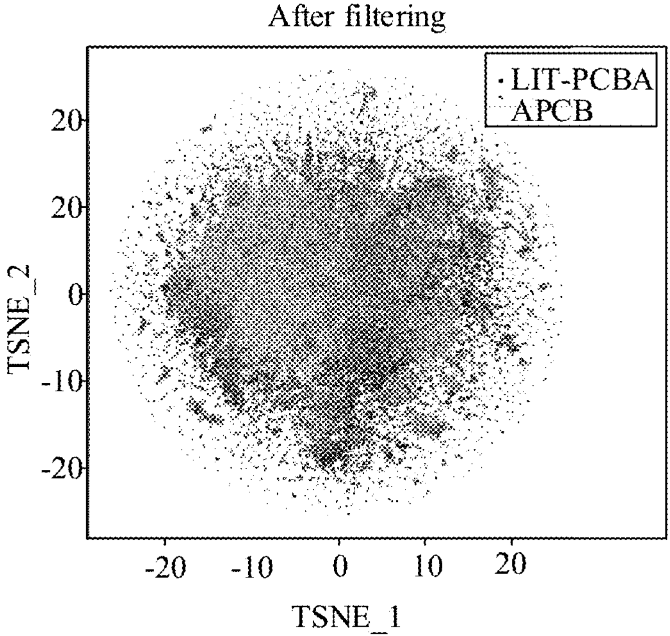
FIG. 9B is a schematic diagram of a chemical structure space of APCB and LIT-PCBA after grid filtering according to an embodiment of this application.

Two-dimensional TSNE vectors of molecules in the data set are calculated and visualized on a two-dimensional plane to obtain FIGS. 9A-9B. FIG. 9A shows a chemical structure space of APCB and LIT-PCBA before grid filtering. FIG. 9B shows a chemical structure space of APCB and LIT-PCBA after grid filtering. Each point represents an organic small molecule (namely, compound), and a closer distance between the points corresponds to higher structural similarity. Before grid filtering, the compounds are not evenly distributed in the chemical space, and a large number of ligands with similar structures are stacked together. After grid filtering, the ligands of APCB in FIG. 9B are evenly distributed and cover more chemical space than the ligands of LIT-PCBA, indicating that APCB had less domain bias than LIT-PCBA.

The internal diversity of APCB and LIT-PCBA data sets is calculated (the internal diversity that is closer to 1 indicates better structural diversity of the molecules in the data sets). The internal diversity of APCB (ALDH1:0.894, MAPK1:0.878) is higher than that of LIT-PCBA (ALDH1: 0.868, MAPK1:0.868), indicating that APCB has higher structural diversity than LIT-PCBA. Therefore, the introduced domain bias is less.

Figure 10:
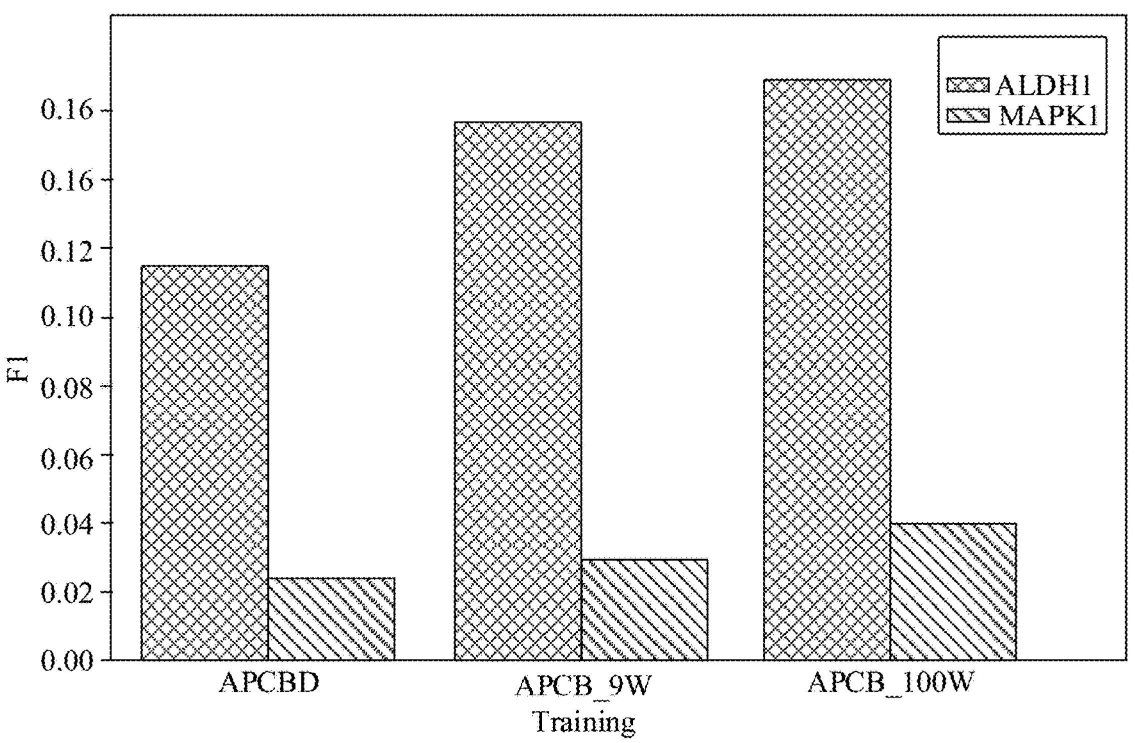
FIG. 10 is a schematic diagram of comparison of model performances trained using data sets filtered by different grid points according to an embodiment of this application.

In order to further validate the influence of grid filtering and grid number, an IGN model is trained on these data sets and tested on the LIT-PCBA test set. The model performance is shown in FIG. 10. For ALDH1 and MAPK1, models trained on the grid-filtered data sets (APCB 9 W and APCB 100 W) are tested on the LIT-PCBA test set, and the performance is better than that of a model trained on the biased data set (APCBD). In a certain range, as the data set size increases, the model performance will also be improved. However, the performance of the model will not be improved as the data size increases, because the analogue bias and the domain bias will be inevitably introduced into an increasing number of data.

The validation of the noncausal bias is as follows.

In the data sets (for example, DUDE and DEKOIS) in the related art, a single noncausal bias is introduced since decoys are collected based on a single hypothesis. Therefore, in APCB, two noncausal biases are introduced, including docking scores and topological structures (Morgan fingerprints) that cancel each other, to force the model to learn active protein ligand binding modes and inactive protein ligand binding modes from the data sets. The APCB data set may be decomposed into a subset (active as decoys (AD)) constituted by decoys conformations generated from the active compound and a subset (physic chemical-based (PCB)) constituted by decoys matching with physicochemical properties generated from the CRNN. AD contains decoys conformations generated from the active ligand, and PCB contains decoys matching with physicochemical properties generated from the CRNN.

Figure 11A:
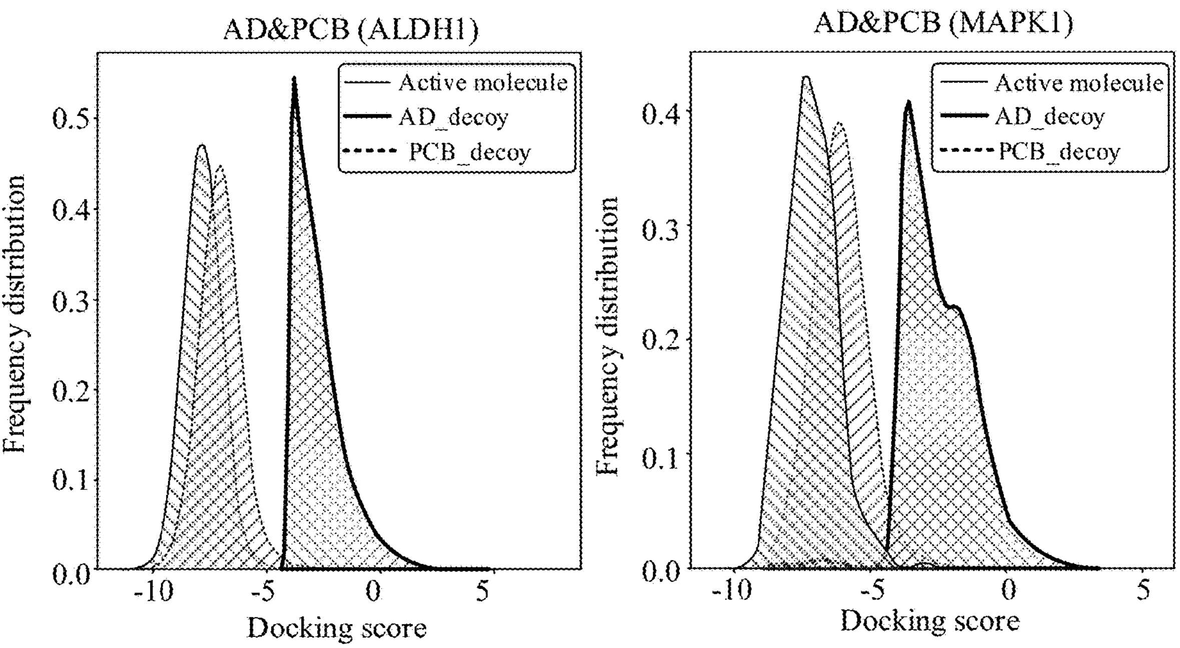
FIG. 11A is a schematic diagram of distribution of docking scores for an AD set and a PCB set for targets (ALDH1, MAPK1) according to an embodiment of this application.

As shown in FIG. 11A, docking scores of decoys and active molecules in the AD data set differ greatly, and the machine learning algorithm can distinguish between positive and negative samples by restoring the docking scores. The model thus trained, while performing well on the AD set, only predicts the binding strength of protein ligands by reducing the docking score rather than learning an interaction mode between the protein ligands. Such a model does not perform well in real application scenarios. Therefore, it is considered that the model learns the noncausal bias from the AD data set.

Figure 11B:
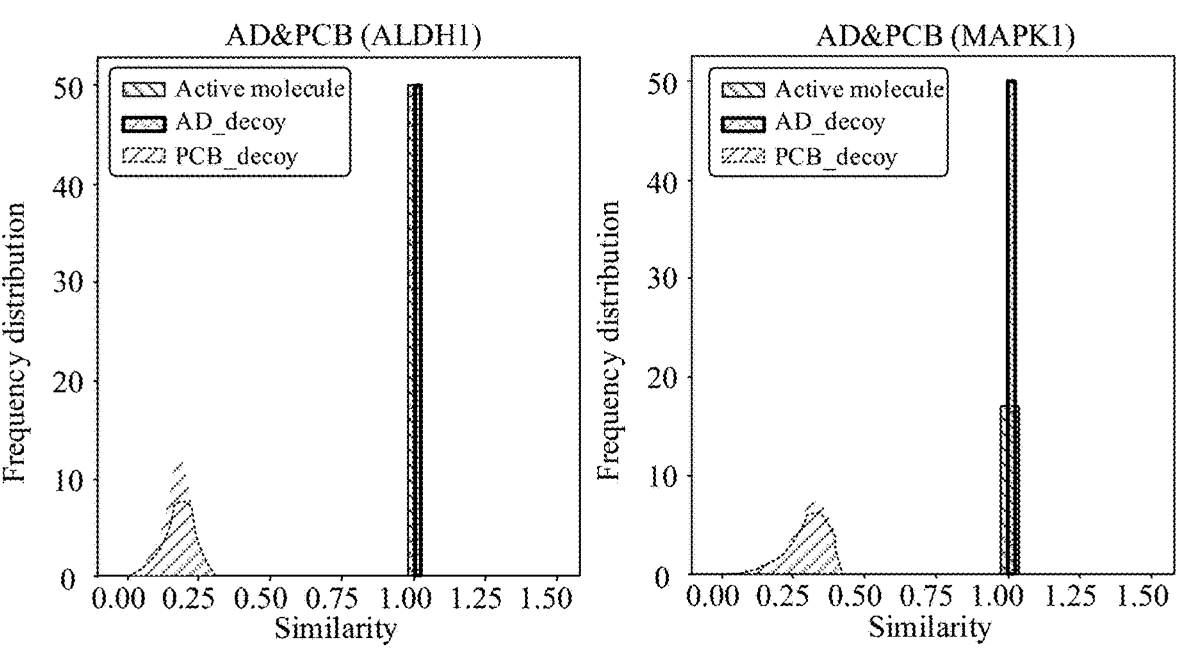
FIG. 11B is a schematic diagram of distribution of topological structure similarity (AD set, PCB set) between decoys and "seed" active ligands of targets (ALDH1, MAPK1) according to an embodiment of this application.

Similarly, if only training is performed on the PCB data set, as shown in FIG. 11B, since the structural similarity of the positive and negative samples in the PCB data set is low, the model will only learn activity prediction based on the structural similarity, namely, learn the noncausal bias in the PCB data set.

Figure 11C:
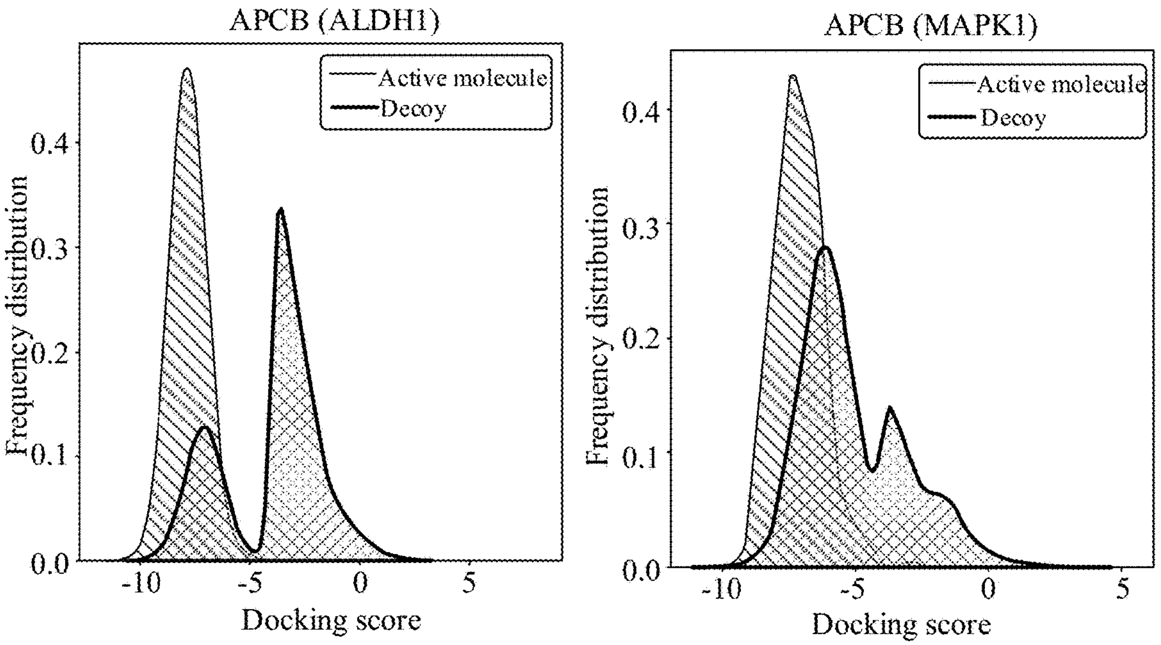
FIG. 11C is a schematic diagram of distribution of docking scores for an APCB 9 W set for targets (ALDH1, MAPK1) according to an embodiment of this application.
Figure 11D:
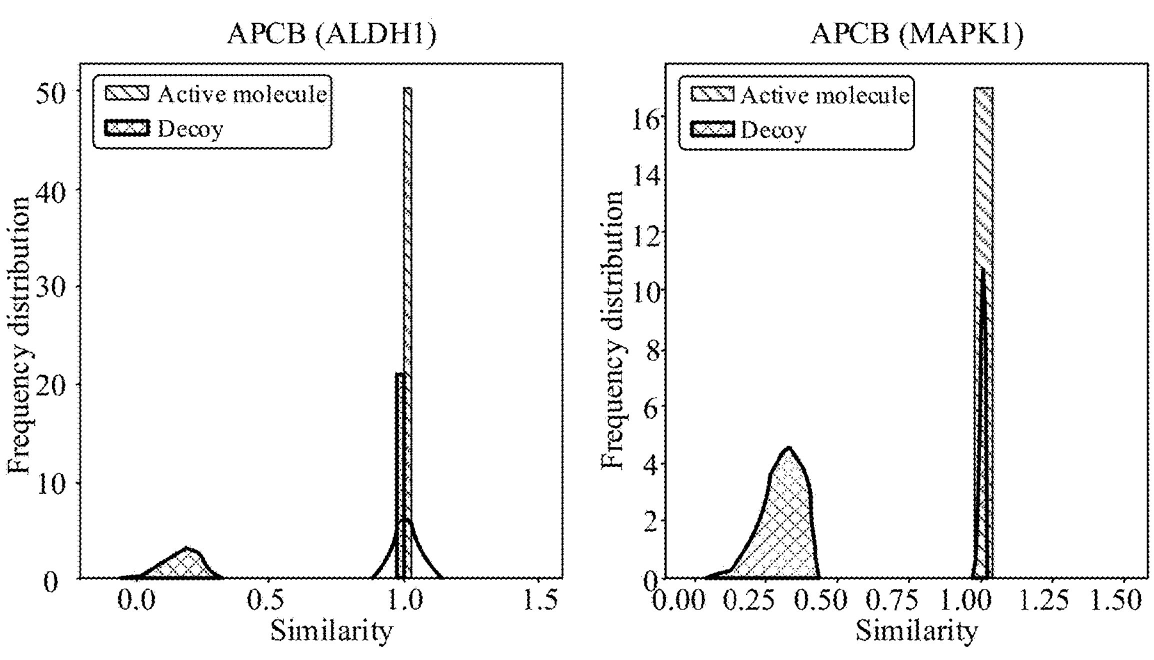
FIG. 11D is a schematic diagram of distribution of topological structure similarity (APCB 9 W set) between decoys and "seed" active ligands of targets (ALDH1, MAPK1) according to an embodiment of this application.

In order to avoid that the model learns the noncausal bias, the AD data set and the PCB data set are combined to form an APCB data set in this embodiment. As shown in FIGS. 11C-11D, when the two data sets are combined together, the boundary of the structural similarity between the positive and negative samples and the difference in the docking scores is eliminated, and the machine learning model cannot accurately classify according to the docking score alone or the structural dissimilarity between the positive and negative samples, thereby avoiding that the model learns the noncausal bias caused by the docking scores and the structural similarity.

Figure 11E:
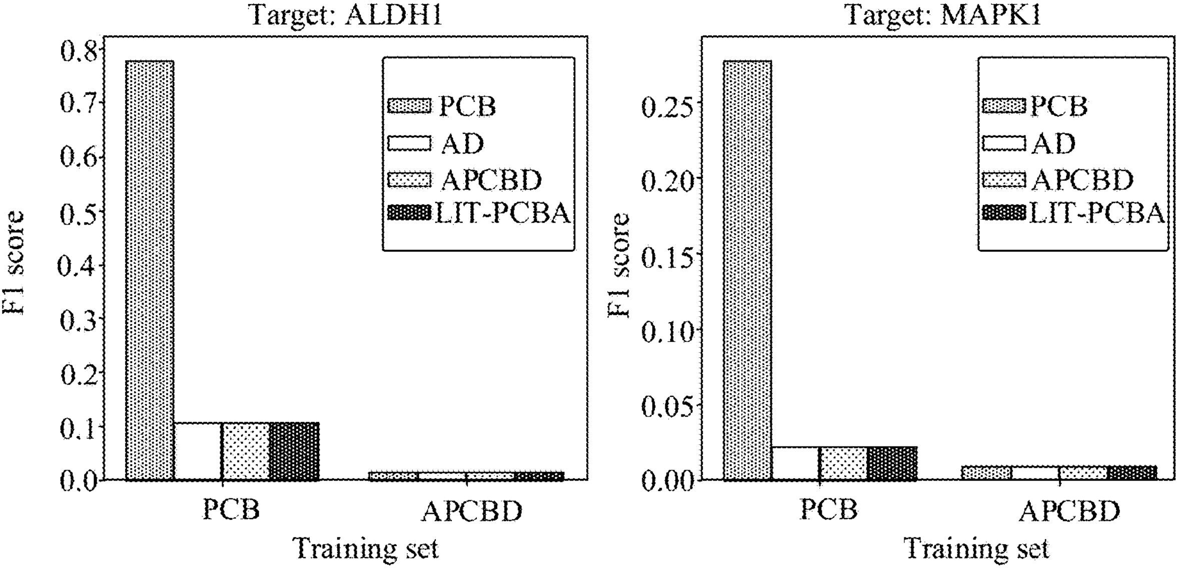
FIG. 11E is a schematic diagram of performance of an ECFP-characterized XGBoost model trained on a PCB set and an APCB data set respectively according to an embodiment of this application.

To further validate, an XGBoost model with energy terms decomposed from Glide SP SF as the input and an XGBoost model with ECFP as the input are trained in this embodiment. When the ECFP fingerprint is used as a descriptor, as shown in FIG. 11E, the XGBoost model can distinguish between active and inactive molecules well on PCB, but cannot perform well on other data sets.

Figure 11F:
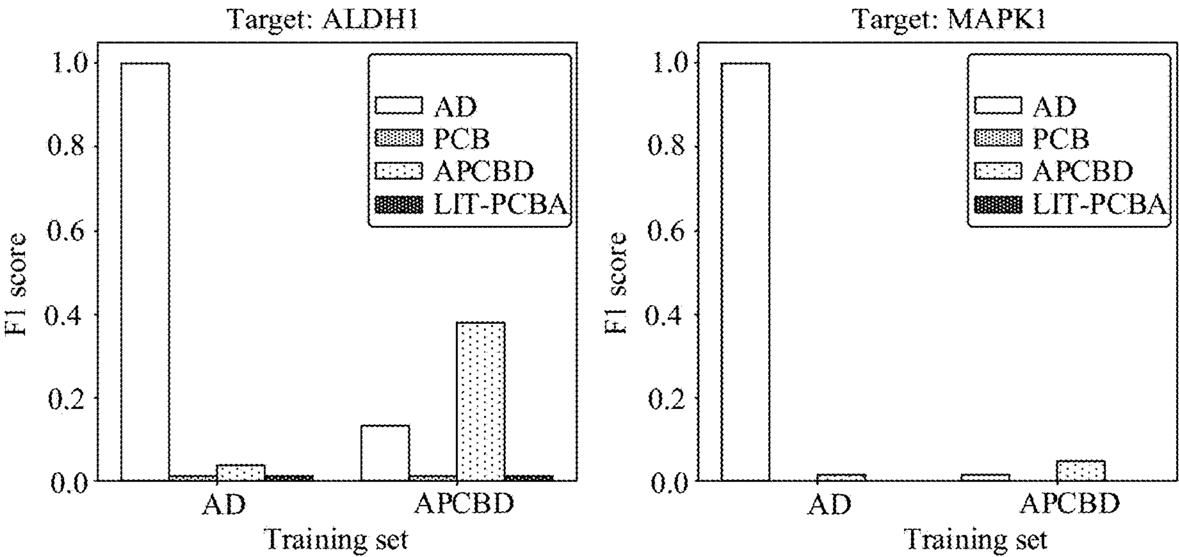
FIG. 11F is a schematic diagram of performance of an XGBoost model characterized by energy terms of a Glide scoring function trained on an AD set and APCBD respectively according to an embodiment of this application.

Also, as shown in FIG. 11F, the XGBoost model with the energy terms as the input shows better performance on the AD subset than other models, but has a poor generalization performance.

When the foregoing two models (XGB-energy term, XGB-ECFP fingerprint) are trained on the APCB data set formed by the AD subset and the PCB subset, the performance will be reduced, indicating that the model learning difficulty is increased and the noncausal bias is reduced by mixing the two noncausal biases.

The performance test of the model based on APCB training in a real scenario is as follows.

After the hidden bias is validated, the performance of the model trained on the APCB data set in the real scenario is validated. Therefore, IGN models are constructed on LIT-PCBA and APCBD, respectively, and tested on each test set in this embodiment. Therefore, the model is tested on an own-test from the same source as the training set and a cross-test from another source.

Figure 12A:
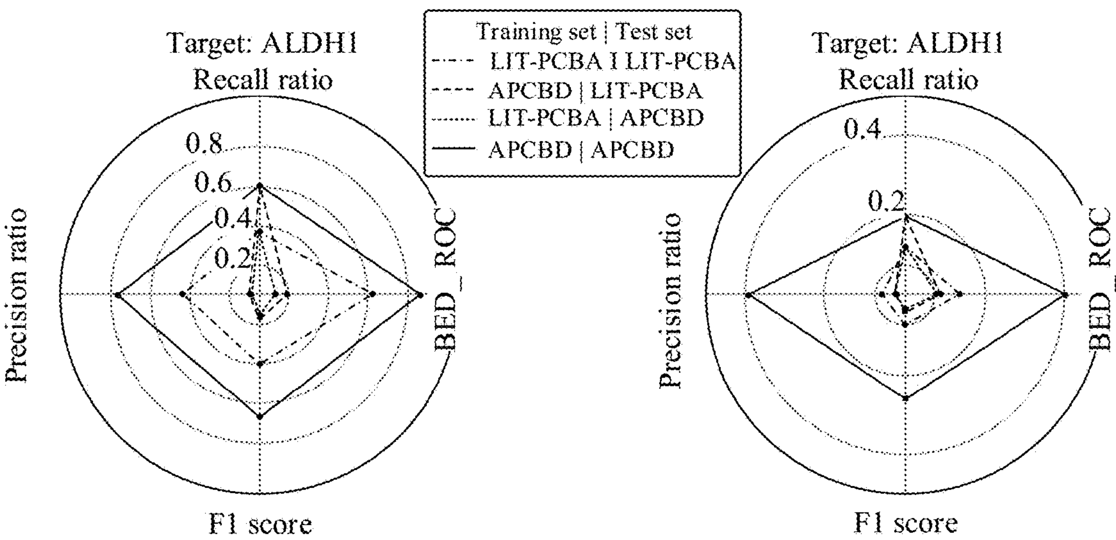
FIG. 12A is a schematic diagram of cross-evaluation performance of IGN trained on LIT-PCBA and APCB data sets respectively according to an embodiment of this application.

As shown in FIG. 12A, when tested in the same manner (both on the cross-test and both on the own-test), the model obtained by APCB training and the model obtained by LIT-PCBA training show similar distributions in the four indicators, indicating that the model trained on the APCB data set has similar performance (prediction accuracy and screening capability) compared to the model trained on the LIT-PCBA data set.

In addition, the model trained on APCBD (ALDH1 of 0.600 and MAPK1 of 0.195) is superior to the model trained on LIT-PCBA (ALDH1 of 0.368 and MAPK1 of 0.117) from the perspective of recall, indicating that the model based on APCB training may find more active ligands from the compound library than the model trained on LIT-PCBA.

To further validate the generalization capability of the model trained on the APCB data set, the model is trained on the PCB data set similar to the DUDE construction method, except for the LIT-PCBA and APCBD models. These models are tested on a homologous test set (current test) and a real-world test set (namely, experimentally validated test set of LIT-PCBA). Good generalization capability means that a model shows good performance on the current test set and achieves comparable performance on the real additional test set.

Figure 12B:
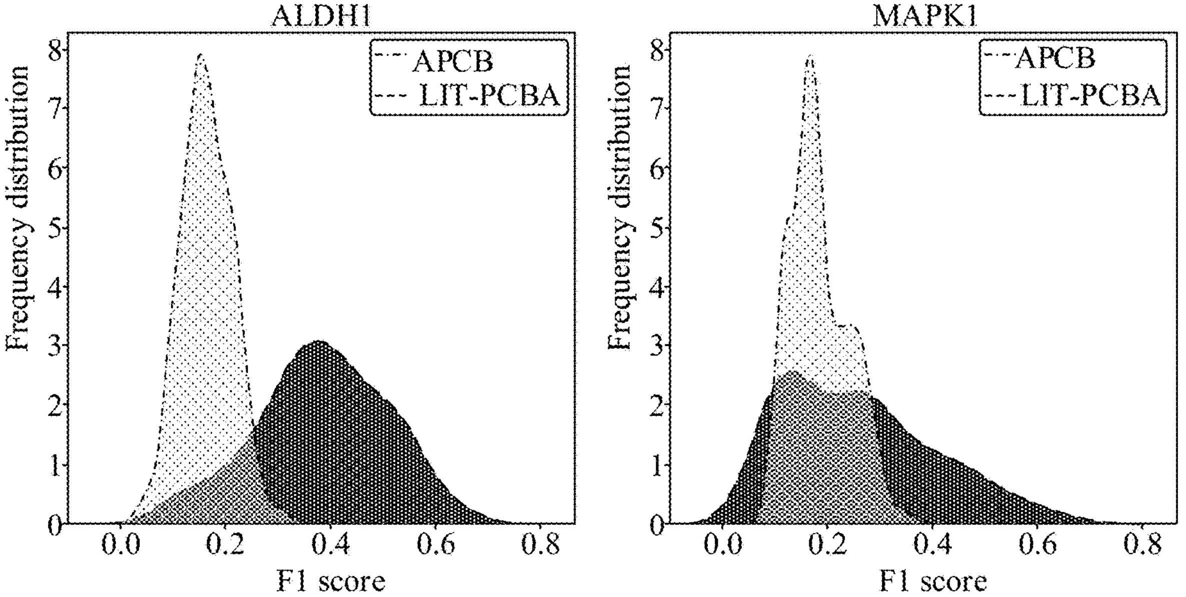
FIG. 12B is a schematic diagram of performance of IGN on test sets having different distributions according to an embodiment of this application.

To further validate whether the data set distribution affects model performance, 100 bootstraps are performed to perturb the distribution of the LIT-PCBA test set and draw a distribution diagram for the model performance as shown in FIG. 12B. As shown in FIG. 12B, the content of model learning and model performance are related to the distribution of the data set. Considering that LIT-PCBA is a limited ligand constructed by PubChem BioAssay, the data distribution of LIT-PCBA may not be the optimal distribution for constructing MLSF with stronger generalization capability. In contrast, a data-sized scalable APCBD with an adjustable data set distribution is suitable for constructing MLSF with generalization capability.

The artificial intelligence-based compound processing method provided in this embodiment has thus far been described in connection with applications and implementations of the server provided in this embodiment. An embodiment of this application also provides a compound processing apparatus. During actual application, functional modules in the compound processing apparatus may be cooperatively implemented by hardware resources of an electronic device (for example, a terminal device, a server or a server cluster), for example, a computing resource such as a processor, and a communication resource (for example being used for supporting implementation of various types of communications such as optical cable communication and cellular communication), and a memory. FIG. 2 shows the compound processing apparatus 555 stored in the memory 550, which may be software in the form of programs and plug-ins, for example, software modules designed in programming languages such as software C/C++ and Java, application software designed in programming languages such as C/C++ and Java, or dedicated software modules, application interfaces, plug-ins, cloud services, and other implementations in a large software system.

The compound processing apparatus 555 includes a series of modules, including an obtaining module 5551, a generation module 5552, a docking module 5553, and a construction module 5554. The following continues to describe the cooperation of various modules in the compound processing apparatus 555 provided in the embodiments of this application to implement a compound processing scheme.

The obtaining module 5551 is configured to obtain an active compound for a target protein. The generation module 5552 is configured to perform compound generation processing on an attribute property of the active compound to obtain a first candidate compound having the attribute property. The docking module 5553 is configured to: perform molecular docking processing on the active compound and the target protein to obtain molecular docking information respectively corresponding to a plurality of molecular conformations of the active compound, screen the plurality of molecular conformations based on the molecular docking information respectively corresponding to the plurality of molecular conformations, and use the screened molecular conformations as a second candidate compound corresponding to the active compound. The construction module 5554 is configured to construct a compound library for the target protein based on the first candidate compound and the second candidate compound.

In some embodiments, the generation module 5552 is further configured to: encode the attribute property of the active compound to obtain a state vector of the attribute property; and perform conditional generation processing on the state vector of the attribute property to obtain the first candidate compound having the attribute property.

In some embodiments, the compound generation processing is achieved by a generation model. The generation model includes at least one first fully-connected layer and at least one second fully-connected layer. The state vector includes a hidden state and a cell state. The generation module 5552 is further configured to: encode the attribute property of the active compound through the first fully-connected layer to obtain the hidden state of the attribute property corresponding to the first fully-connected layer; and encode the attribute property of the active compound through the second fully-connected layer to obtain the cell state of the attribute property corresponding to the second fully-connected layer.

In some embodiments, the generation module 5552 is further configured to perform the following processing through the first fully-connected layer: performing vector transformation processing on the attribute property of the active compound to obtain a transformed vector of the attribute property; and mapping the transformed vector of the attribute property to obtain the hidden state of the attribute property corresponding to the first fully-connected layer.

In some embodiments, the compound generation processing is achieved by a generation model. The generation model includes a plurality of cascaded memory layers. The generation module 5552 is further configured to: perform cascaded decoding processing on the state vector of the attribute property through the plurality of cascaded memory layers to obtain element vectors corresponding to the attribute property; and combine elements corresponding to the element vectors according to a generation order of the element vectors to obtain the first candidate compound having the attribute property.

In some embodiments, the generation module 5552 is further configured to perform the following processing through the plurality of cascaded memory layers: performing cascaded decoding processing on the state vector of the attribute property and a start vector to obtain a first element vector corresponding to the attribute property; and performing cascaded decoding processing on the state vector of the attribute property and an $i^{th}$ element vector to obtain an $i+1^{th}$ element vector corresponding to the attribute property. i is an increasing natural number, $1 \le i \le N$. N is the number of element vectors corresponding to the attribute property.

In some embodiments, the generation module 5552 is further configured to: decode the state vector of the attribute property corresponding to the first memory layer and the start vector through the first memory layer in the plurality of cascaded memory layers; output a decoding result of the first memory layer to a memory layer cascaded thereto, and continue to perform decoding processing and decoding result output through the memory layer cascaded thereto, until a decoding result is outputted to the last memory layer; and map a decoding result outputted by the last memory layer to obtain the first element vector corresponding to the attribute property.

In some embodiments, the generation module 5552 is further configured to: decode, through a $j^{th}$ memory layer in the plurality of cascaded memory layers, the state vector of the attribute property corresponding to the $j^{th}$ memory layer and a decoding result outputted by a $j-1^{th}$ memory layer to obtain a decoding result of the $j^{th}$ memory layer; and output the decoding result of the $i^{th}$ memory layer to a decoding result of a $j+1^{th}$ memory layer. j is an increasing natural number, $1<j<M$. M is the number of the memory layers.

In some embodiments, the generation module 5552 is further configured to: perform forget gate-based forget processing on the cell state of the attribute property corresponding to the $i^{th}$ memory layer, the hidden state of the attribute property, and the decoding result outputted by the $j-1^{th}$ memory layer, to obtain a forget vector of the $j^{th}$ memory layer; perform update gate-based memory update processing on the forget vector of the $j^{th}$ memory layer, the hidden state of the attribute property, and the decoding result outputted by the $j-1^{th}$ memory layer, to obtain the updated cell state corresponding to the $j^{th}$ memory layer; and map the hidden state of the attribute property, the decoding result outputted by the $j-1^{th}$ memory layer, and the updated cell state to obtain the decoding result of the $j^{th}$ memory layer.

In some embodiments, the generation module 5552 is further configured to: decode the updated cell state corresponding to the first memory layer, the mapped hidden state corresponding to the first memory layer, and the $i^{th}$ element vector through the first memory layer in the plurality of cascaded memory layers; output a decoding result of the first memory layer to a memory layer cascaded thereto, and continue to perform decoding processing and decoding result output through the memory layer cascaded thereto, until a decoding result is outputted to the last memory layer; and map a decoding result outputted by the last memory layer to obtain the $i+1^{th}$ element vector corresponding to the attribute property.

In some embodiments, the docking module 5553 is further configured to: perform molecular dynamics simulation processing on the target protein to obtain a binding pocket of the target protein; structurally adjust the target protein to obtain the adjusted target protein; and dock the adjusted target protein to the binding pocket of the target protein to obtain the molecular docking information respectively corresponding to the plurality of molecular conformations of the active compound.

In some embodiments, the docking module 5553 is further configured to: repair side chains and ring structures in the target protein to obtain the repaired target protein; adjust bond orders and formal charges of the repaired target protein to obtain the adjusted target protein; and perform force field optimization processing on the direction of hydrogen atoms of the adjusted target protein to obtain the adjusted target protein.

In some embodiments, the construction module 5554 is further configured to: map a molecular fingerprint of the first candidate compound to obtain a two-dimensional vector of the first candidate compound; perform grid filtering processing on the first candidate compound based on the two-dimensional vector of the first candidate compound to obtain the filtered first candidate compound; and construct the compound library for the target protein based on the second candidate compound and the filtered first candidate compound.

In some embodiments, the construction module 5554 is further configured to: construct a two-dimensional chemical space having a plurality of grids based on the two-dimensional vector of the first candidate compound; map the first candidate compound to the two-dimensional chemical space; and filter the first candidate compound in the two-dimensional chemical space based on an accommodation space of each of the grids to obtain the filtered first candidate compound.

An embodiment of this application provides a computer program product or computer program. The computer program product or computer program includes computer instructions. The computer instructions are stored in a computer-readable storage medium. A processor of a computer device reads the computer instructions from the computer-readable storage medium. The processor executes the computer instructions, so as to enable the computer device to perform the artificial intelligence-based compound processing method according to the foregoing embodiment of this application.

An embodiment of this application provides a computer-readable storage medium storing executable instructions. The executable instructions are stored therein. When executed by a processor, the executable instructions may trigger the processor to perform the artificial intelligence-based compound processing method according to the foregoing embodiment of this application, for example, the artificial intelligence-based compound processing method shown in FIGS. 3A-3B.

In some embodiments, the computer-readable storage medium may be a memory such as FRAM, ROM, PROM, EPROM, EEPROM, flash memory, magnetic surface memory, optical disc, or CD-ROM. Various devices including one or any combination of the foregoing memories are also possible.

The flowcharts and block diagrams in the accompanying drawings illustrate possible system architectures, functions, and operations that may be implemented by the system, method, and computer program product according to various embodiments of this application. In this regard, each box in a flowchart or a block diagram may represent a module, a program segment, or a part of code. The module, the program segment, or the part of code includes at least one executable instruction used for implementing designated logic functions. In some embodiments, functions described in boxes may alternatively occur in a sequence different from what were described in an accompanying drawing. For example, two steps described in boxes shown in succession may be performed in parallel, and sometimes the steps in two boxes may be performed in a reverse sequence. This is determined by a related function. Each box in a block diagram and/or a flowchart, and a combination of boxes in the block diagram and/or the flowchart, may be implemented with a dedicated hardware-based system that performs specified functions or operations, or may be implemented with a combination of dedicated hardware and computer instructions.

Each module/unit in various disclosed embodiments can be integrated in a processing unit, or each module/unit can exist separately and physically, or two or more modules/units can be integrated in one unit. The modules/units as disclosed herein can be implemented in the form of hardware (e.g., processing circuitry and/or memory) or in the form of software functional unit(s) (e.g., developed using one or more computer programming languages), or a combination of hardware and software.

In some embodiments, the executable instructions may take the form of program, software, software module, script, or code, may be written in any form of programming language (including compiled or interpreted languages, or declarative or procedural languages), and may be deployed in any form, including as a stand-alone program or as a module, component, subroutine, or another unit suitable for use in a computing environment.

By way of example, the executable instructions may, but need not, correspond to files in a file system, and may be stored in a portion of a file that stores other programs or data, for example, in one or more scripts in a hyper text markup language (HTML) document, in a single file dedicated to the program in question, or in a plurality of coordinated files (for example, files that store one or more modules, subroutines, or portions of code).

By way of example, the executable instructions may be deployed to be executed on one computing device, or on a plurality of computing devices located at one site, or on a plurality of computing devices distributed across multiple sites and interconnected by a communication network.

The foregoing descriptions are merely embodiments of this application and are not intended to limit the protection scope of this application. Any modification, equivalent replacement, or improvement made without departing from the spirit and principle of this application shall fall within the protection scope of this application.

What is claimed is:

1. An artificial intelligence-based compound processing method, applied to an electronic device, the method comprising:

obtaining an active compound for a target protein;

performing compound generation processing on an attribute property of the active compound to obtain a first candidate compound;

performing molecular docking processing on the active compound and the target protein to obtain molecular docking information respectively corresponding to a plurality of molecular conformations of the active compound;

screening the plurality of molecular conformations based on the molecular docking information respectively to identify a second candidate compound corresponding to the active compound;

mapping a molecular fingerprint of the first candidate compound to obtain a two-dimensional vector of the first candidate compound;

constructing a two-dimensional chemical space having a plurality of grids based on the two-dimensional vector of the first candidate compound;

mapping the first candidate compound to the two-dimensional chemical space;

filtering the first candidate compound in the two-dimensional chemical space based on the accommodating space of each grid to obtain the filtered first candidate compound; and constructing a library of compounds for the target protein based on the filtered first candidate compound and the second candidate compound.

2. The method according to claim 1, wherein the performing compound generation processing on an attribute property of the active compound to obtain a first candidate compound comprises:

encoding the attribute property of the active compound to obtain a state vector of the attribute property; and performing conditional generation processing on the state vector of the attribute property to obtain the first candidate compound having the attribute property.

3. The method according to claim 2, wherein the compound generation processing is based on a generation model, the generation model comprising at least one first fully-connected layer and at least one second fully-connected layer;

the state vector comprises a hidden state and a cell state; and the encoding the attribute property of the active compound to obtain a state vector of the attribute property comprises:

encoding the attribute property of the active compound through the first fully-connected layer to obtain the hidden state of the attribute property corresponding to the first fully-connected layer; and encoding the attribute property of the active compound through the second fully-connected layer to obtain the cell state of the attribute property corresponding to the second fully-connected layer.

4. The method according to claim 3, wherein the encoding the attribute property of the active compound through the first fully-connected layer to obtain the hidden state of the attribute property corresponding to the first fully-connected layer comprises:

performing vector transformation processing on the attribute property of the active compound to obtain a transformed vector of the attribute property through the first fully-connected layer; and mapping the transformed vector of the attribute property to obtain the hidden state of the attribute property corresponding to the first fully-connected layer through the first fully-connected layer.

5. The method according to claim 2, wherein the compound generation processing is based on a generation model, the generation model comprising a plurality of cascaded memory layers;

the performing conditional generation processing on the state vector of the attribute property to obtain the first candidate compound having the attribute property comprises:

performing cascaded decoding processing on the state vector of the attribute property through the plurality of cascaded memory layers to obtain element vectors corresponding to the attribute property; and combining elements corresponding to the element vectors according to a generation order of the element vectors to obtain the first candidate compound having the attribute property.

6. The method according to claim 5, wherein the performing cascaded decoding processing on the state vector of the attribute property through the plurality of cascaded memory layers to obtain element vectors corresponding to the attribute property comprises:

performing the following processing through the plurality of cascaded memory layers:

performing cascaded decoding processing on the state vector of the attribute property and a start vector to obtain a first element vector corresponding to the attribute property; and performing cascaded decoding processing on the state vector of the attribute property and an $i^{th}$ element vector to obtain an $i+1^{th}$ element vector corresponding to the attribute property, i being an increasing natural number, $1 \leq i < N$, N being the number of element vectors corresponding to the attribute property.

7. The method according to claim 6, wherein the performing cascaded decoding processing on the state vector of the attribute property and a start vector to obtain a first element vector corresponding to the attribute property comprises:

decoding the state vector of the attribute property corresponding to the first memory layer and the start vector through the first memory layer in the plurality of cascaded memory layers;

outputting a decoding result of the first memory layer to a memory layer cascaded, and continuing to perform decoding processing and decoding result output through the memory layer cascaded, until a decoding result is outputted to the last memory layer; and mapping a decoding result outputted by the last memory layer to obtain the first element vector corresponding to the attribute property.

8. The method according to claim 7, wherein the continuing to perform decoding processing and decoding result output through the memory layer cascaded comprises:

decoding, through a $j^{th}$ memory layer in the plurality of cascaded memory layers, the state vector of the attribute property corresponding to the $j^{th}$ memory layer and a decoding result outputted by a $j-1^{th}$ memory layer to obtain a decoding result of the $j^{th}$ memory layer; and outputting the decoding result of the $j^{th}$ memory layer to a decoding result of a $j+1^{th}$ memory layer, j being an increasing natural number, $1<j<M$, M being the number of the memory layers.

9. The method according to claim 8, wherein the decoding the state vector of the attribute property corresponding to the $j^{th}$ memory layer and a decoding result outputted by a $j-1^{th}$ memory layer to obtain a decoding result of the $j^{th}$ memory layer comprises:

performing forget gate-based forget processing on the cell state of the attribute property corresponding to the $j^{th}$ memory layer, the hidden state of the attribute property, and the decoding result outputted by the $j-1^{th}$ memory layer, to obtain a forget vector of the $j^{th}$ memory layer;

performing update gate-based memory update processing on the forget vector of the $j^{th}$ memory layer, the hidden state of the attribute property, and the decoding result outputted by the $j-1^{th}$ memory layer, to obtain the updated cell state corresponding to the $j^{th}$ memory layer; and mapping the hidden state of the attribute property, the decoding result outputted by the j−1 t memory layer, and the updated cell state to obtain the decoding result of the $i^{th}$ memory layer.

10. The method according to claim 9, wherein the performing cascaded decoding processing on the state vector of the attribute property and an $i^{th}$ element vector to obtain an $i+1^{th}$ element vector corresponding to the attribute property comprises:

decoding the updated cell state corresponding to the first memory layer, the mapped hidden state corresponding to the first memory layer, and the $i^{th}$ element vector through the first memory layer in the plurality of cascaded memory layers;

outputting a decoding result of the first memory layer to a memory layer cascaded, and continuing to perform decoding processing and decoding result output through the memory layer cascaded, until a decoding result is outputted to the last memory layer; and mapping a decoding result outputted by the last memory layer to obtain the $i+1^{th}$ element vector corresponding to the attribute property.

11. The method according to claim 1, wherein the performing molecular docking processing on the active compound and the target protein to obtain molecular docking information respectively corresponding to a plurality of molecular conformations of the active compound comprises:

performing molecular dynamics simulation processing on the target protein to obtain a binding pocket of the target protein;

structurally adjusting the target protein to obtain the adjusted target protein; and docking the adjusted target protein to the binding pocket of the target protein to obtain the molecular docking information respectively corresponding to the plurality of molecular conformations of the active compound.

12. The method according to claim 11, wherein the structurally adjusting the target protein to obtain the adjusted target protein comprises:

repairing side chains and ring structures in the target protein to obtain the repaired target protein;

adjusting bond orders and formal charges of the repaired target protein to obtain the adjusted target protein; and performing force field optimization processing on the direction of hydrogen atoms of the adjusted target protein to obtain the adjusted target protein.

13. An electronic device, comprising:

a memory, configured to store executable instructions; and a processor, configured, when executing the executable instructions stored in the memory, to implement:

obtaining an active compound for a target protein;

performing compound generation processing on an attribute property of the active compound to obtain a first candidate compound;

performing molecular docking processing on the active compound and the target protein to obtain molecular docking information respectively corresponding to a plurality of molecular conformations of the active compound;

screening the plurality of molecular conformations based on the molecular docking information respectively to identify a second candidate compound corresponding to the active compound;

mapping a molecular fingerprint of the first candidate compound to obtain a two-dimensional vector of the first candidate compound;

constructing a two-dimensional chemical space having a plurality of grids based on the two-dimensional vector of the first candidate compound;

mapping the first candidate compound to the two-dimensional chemical space;

filtering the first candidate compound in the two-dimensional chemical space based on the accommodating space of each grid to obtain the filtered first candidate compound; and constructing a library of compounds for the target protein based on the filtered first candidate compound and the second candidate compound.

14. The electronic device according to claim 13, wherein the performing compound generation processing on an attribute property of the active compound to obtain a first candidate compound comprises:

encoding the attribute property of the active compound to obtain a state vector of the attribute property; and performing conditional generation processing on the state vector of the attribute property to obtain the first candidate compound having the attribute property.

15. A non-transitory computer-readable storage medium, storing executable instructions, when executed by a processor, the executable instructions causing the processor to implement:

obtaining an active compound for a target protein;

performing compound generation processing on an attribute property of the active compound to obtain a first candidate compound;

performing molecular docking processing on the active compound and the target protein to obtain molecular docking information respectively corresponding to a plurality of molecular conformations of the active compound;

screening the plurality of molecular conformations based on the molecular docking information respectively to identify a second candidate compound corresponding to the active compound;

mapping a molecular fingerprint of the first candidate compound to obtain a two-dimensional vector of the first candidate compound;

constructing a two-dimensional chemical space having a plurality of grids based on the two-dimensional vector of the first candidate compound;

mapping the first candidate compound to the two-dimensional chemical space;

filtering the first candidate compound in the two-dimensional chemical space based on the accommodating space of each grid to obtain the filtered first candidate compound; and constructing a library of compounds for the target protein based on the filtered first candidate compound and the second candidate compound.

16. The computer-readable storage medium according to claim 15, wherein the performing compound generation processing on an attribute property of the active compound to obtain a first candidate compound comprises:

encoding the attribute property of the active compound to obtain a state vector of the attribute property; and performing conditional generation processing on the state vector of the attribute property to obtain the first candidate compound having the attribute property.

17. The computer-readable storage medium according to claim 16, wherein the compound generation processing is based on a generation model, the generation model comprising at least one first fully-connected layer and at least one second fully-connected layer;

the state vector comprises a hidden state and a cell state; and the encoding the attribute property of the active compound to obtain a state vector of the attribute property comprises:

encoding the attribute property of the active compound through the first fully-connected layer to obtain the hidden state of the attribute property corresponding to the first fully-connected layer; and encoding the attribute property of the active compound through the second fully-connected layer to obtain the cell state of the attribute property corresponding to the second fully-connected layer.

18. The computer-readable storage medium according to claim 17, wherein the encoding the attribute property of the active compound through the first fully-connected layer to obtain the hidden state of the attribute property corresponding to the first fully-connected layer comprises:

performing vector transformation processing on the attribute property of the active compound to obtain a transformed vector of the attribute property through the first fully-connected layer; and mapping the transformed vector of the attribute property to obtain the hidden state of the attribute property corresponding to the first fully-connected layer through the first fully-connected layer.

* * * * *